(12) United States Patent
Kurnik et al.

(10) Patent No.: US 7,991,562 B2
(45) Date of Patent: *Aug. 2, 2011

(54) PCR ELBOW DETERMINATION USING CURVATURE ANALYSIS OF A DOUBLE SIGMOID

(75) Inventors: Ronald T. Kurnik, Foster City, CA (US); Jianmei Wang, Mountain View, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 1352 days.

This patent is subject to a terminal disclaimer.

(21) Appl. No.: 11/533,291

(22) Filed: Sep. 19, 2006

(65) Prior Publication Data
US 2007/0143070 A1 Jun. 21, 2007

Related U.S. Application Data

(63) Continuation-in-part of application No. 11/316,315, filed on Dec. 20, 2005, now Pat. No. 7,668,663.

(51) Int. Cl.
*G01N 33/48* (2006.01)
(52) U.S. Cl. ........................................ 702/19
(58) Field of Classification Search ...................... 702/19
See application file for complete search history.

(56) References Cited

U.S. PATENT DOCUMENTS
2007/0143385 A1  6/2007 Kurnik et al.
2008/0033701 A1  2/2008 Kurnik FOREIGN PATENT DOCUMENTS
| WO | WO 97/46707 A2 | 12/1997 |
| WO | WO 97/46707 A3 | 12/1997 |
| WO | WO 97/46712 A2 | 12/1997 |
| WO | WO 97/46712 A3 | 12/1997 |
| WO | WO 97/46714 A1 | 12/1997 |

OTHER PUBLICATIONS

Bièche, I. et al., "Quantitation of *MYC* Gene Expression in Sporadic Breast Tumors With a Real-Time Reverse Transcription-PCR Assay," *Cancer Research*, Jun. 15, 1999, vol. 59, pp. 2759-2765.
Gibson, U.E.M. et al., "A Novel Method for Real Time Quantitative RT-PCR," *Genome Research*, 1996, vol. 6, pp. 995-1001.
Wang, S-S. et al., "Homogenous Real-Time Detection of Single-Nucleotide Polymorphisms by Strand Displacement Amplification on the BD ProbeTec ET System," *Clinical Chemistry*, 2003, vol. 49, No. 10, pp. 1599-1607.
Weusten, J.J.A.M. et al., "Principles of Quantitation of Viral Loads Using Nucleic Acid Sequence-Based Amplification in Combination With Homogeneous Detection Using Molecular Beacons," *Nucleic Acids Research*, 2002, vol. 30, No. 6, e26, seven pages.
Kurnik, R.T. et al., "Application of the Mixtures of Experts Algorithm for Signal Processing in a Noninvasive Glucose Monitoring System," *Sensors and Actuators B*, 1999, vol. 60, pp. 19-26.
Lourakis, M.I.A., "A Brief Description of the Levenberg-Marquardt Algorithm Implemened by levmar," Feb. 11, 2005, pp. 1-6.
McLauchlan, P., "Robust Observations," located at <http://gandalf-library.sourceforge.net/tutorial/report/node131.html>, Mar. 17, 2006, last visited on Jan. 25, 2008, two pages.
Motulsky, H. et al., *Fitting Models to Biological Data Using Linear and Nonlinear Regression, Version 4.0*, GraphPad Software, Inc., 2003, pp. 3-11 (Table of Contents Only).
Motulsky, H., *Statistics Guide Statistical Analyses for Laboratory and Clinical Researchers, Version 4.0*, GraphPad Software, Inc., Feb. 2005, six pages (Table of Contents Only).
Weisstein, E., "Cubic Spline," located at <http://mathwolrd.wolfram.com/CubicSpine.html>, 1999, last visited on Jan. 25, 2008, four pages.
Cambridge University Press, "Root Finding and Nonlinear Sets of Equations," Chapter 9 in *Numerical Recipes in C: The Art of scientific Computing*, 1988-1992, pp. 347-369.
Tichopad et al., Improving Quantitative Real-Time RT-PCR Reproducibility by Boosting Primer-Linked Amplification Efficiency, Biotechnology Letters 2002, pp. 2053-2056, vol. 24, Kluwer Academic Publishers, The Netherlands.
Kacena et al., Bacterial Growth in Space Flight: Logistic Growth Curve Parameters for *Excherichia coli* and *Bacillus subtilis*, Applied Microbiology and Biotechnology, 1999, pp. 2- 7, vol. 51, Issue 2, Springer-Verlag.
Bassukas, Use of the Recursion Formula of the Gompertz Survival Function to Evaluate Life-Table Data, Mechanisms of Aging and Development, 1996, pp. 155-163, vol. 89, Elsevier Science, Ireland.

*Primary Examiner* — Jerry Lin
(74) *Attorney, Agent, or Firm* — Kilpatrick Townsend and Stockton LLP; Gerald T. Gray

(57) ABSTRACT

Systems and methods for determining characteristic transition values such as elbow values in sigmoid or growth-type curves, such as the cycle threshold (Ct) value in PCR amplification curves. A double sigmoid function with parameters determined by a Levenberg-Marquardt (LM) regression process is used to find an approximation to a curve that fits a PCR dataset. Once the parameters have been determined, the curve can be normalized using one or more of the determined parameters. After normalization, the normalized curve is processed to determine the curvature of the curve at some or all points along the curve, e.g., to produce a dataset or plot representing the curvature v. the cycle number. The cycle number at which the maximum curvature occurs corresponds to the Ct value. The Ct value is then returned and may be displayed or otherwise used for further processing.

46 Claims, 17 Drawing Sheets

FIG. 1
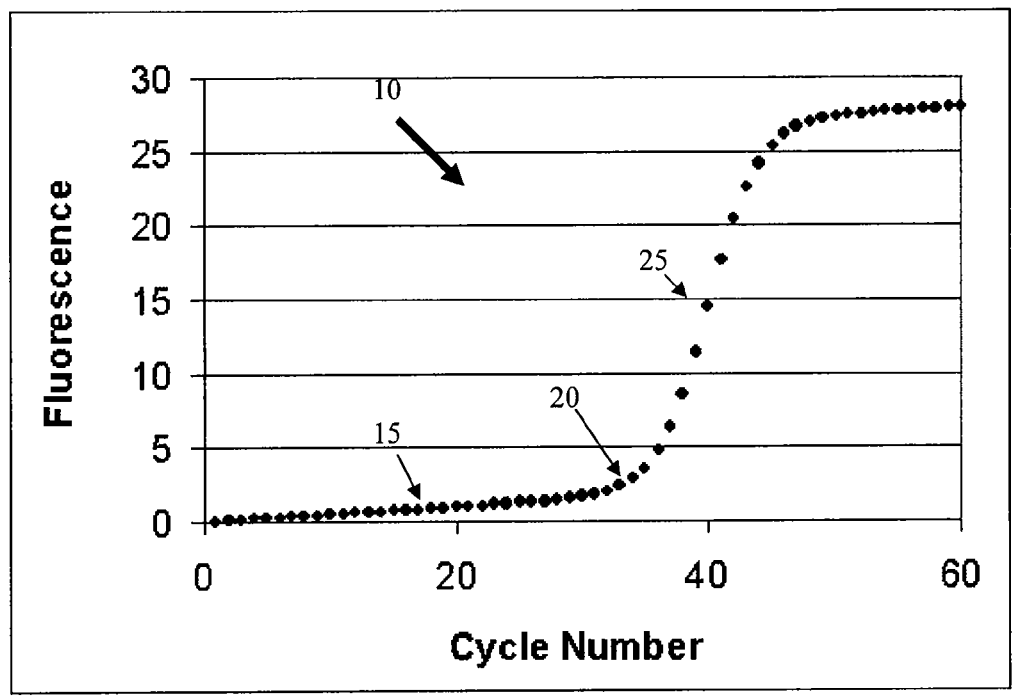
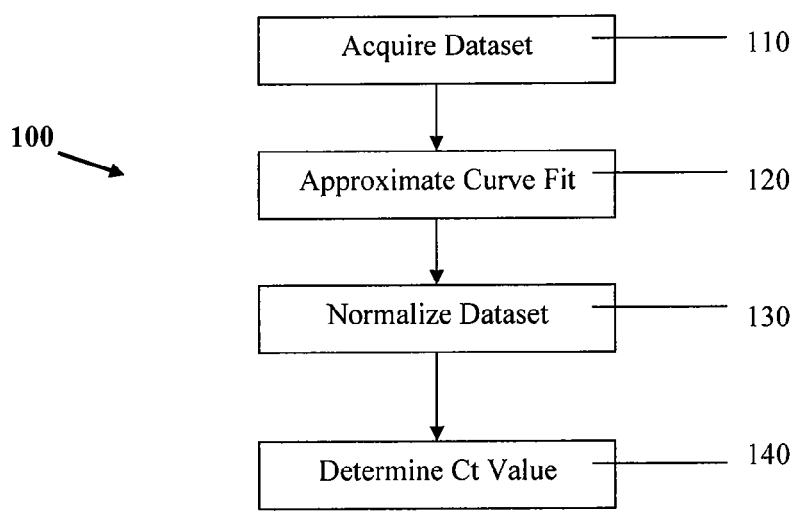
FIG. 2

FIG. 4: Double sigmoid decomposition
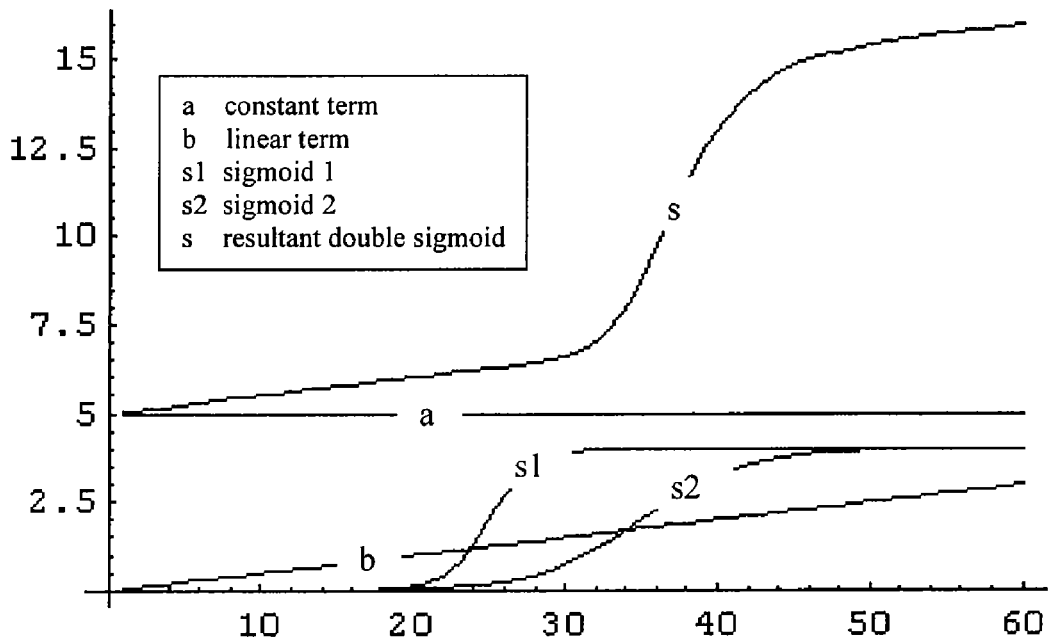
a  constant term
b  linear term
s1  sigmoid 1
s2  sigmoid 2
s  resultant double sigmoid
FIG. 5: The parameters of a sigmoid
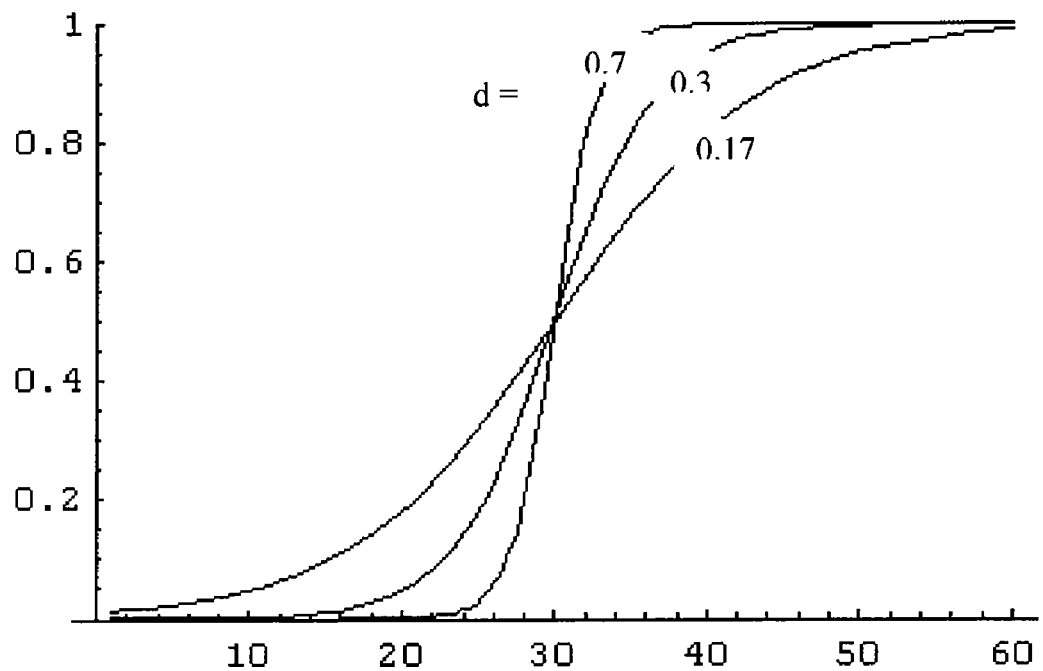

FIG. 6: Initial parameters shapes
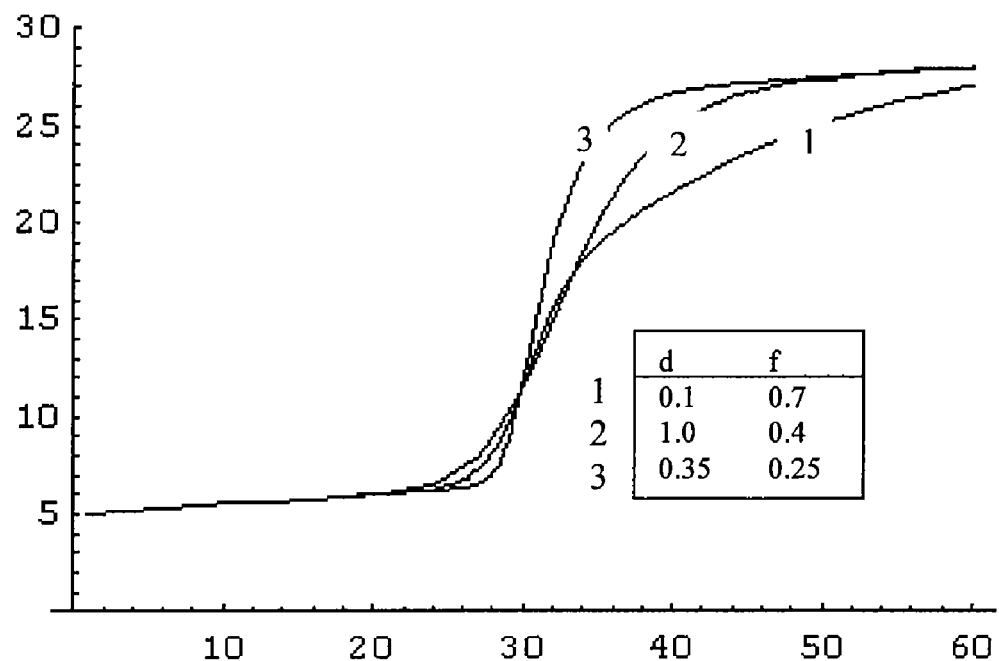

FIG. 10a: PCR data
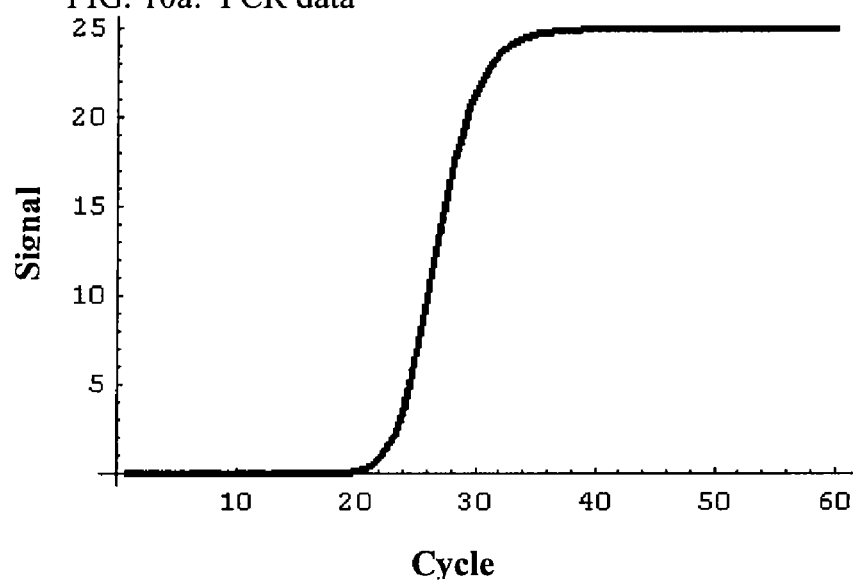
FIG. 10b: Curvature
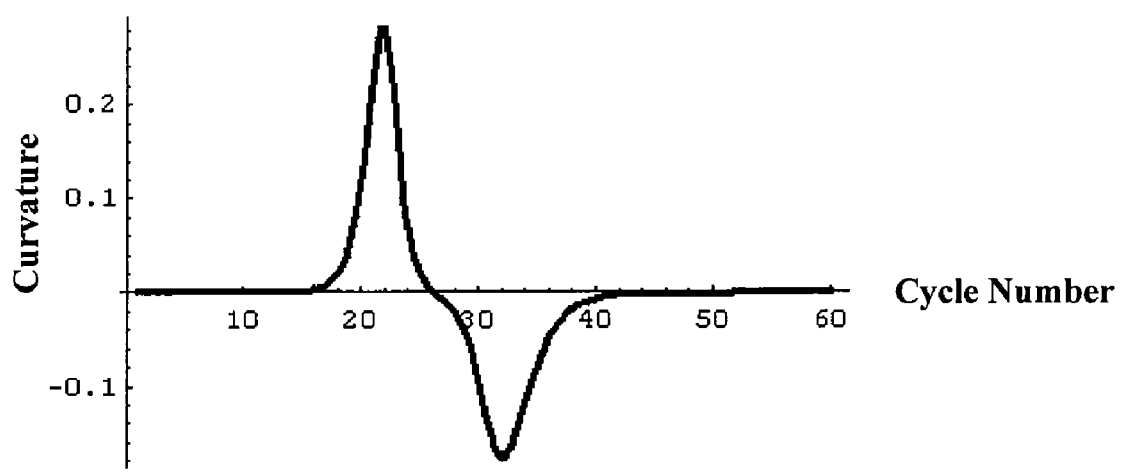

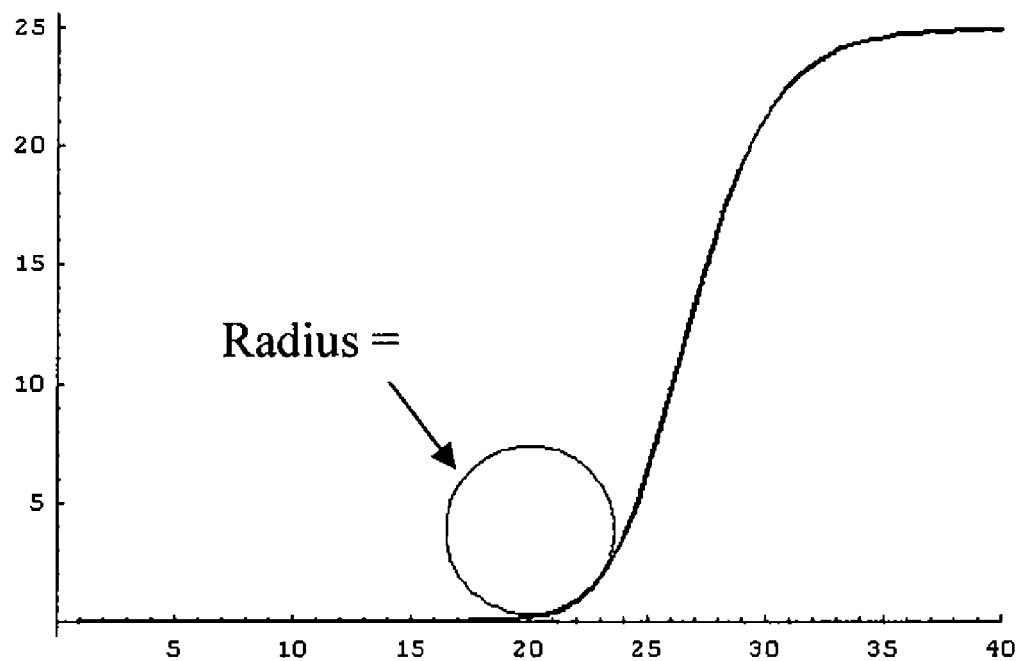
FIG. 11: Radius of Curvature

| Cycle Number | Signal |
|---|---|
| 1 | 1.47 |
| 2 | 1.52 |
| 3 | 1.52 |
| 4 | 1.53 |
| 5 | 1.52 |
| 6 | 1.51 |
| 7 | 1.54 |
| 8 | 1.52 |
| 9 | 1.55 |
| 10 | 1.51 |
| 11 | 1.60 |
| 12 | 1.57 |
| 13 | 1.60 |
| 14 | 1.59 |
| 15 | 1.57 |
| 16 | 1.64 |
| 17 | 1.63 |
| 18 | 1.63 |
| 19 | 1.68 |
| 20 | 1.60 |
| 21 | 1.69 |
| 22 | 1.70 |
| 23 | 1.63 |
| 24 | 1.76 |
| 25 | 1.71 |
| 26 | 1.74 |
| 27 | 1.70 |
| 28 | 1.68 |
| 29 | 1.81 |
| 30 | 1.81 |
| 31 | 1.82 |
| 32 | 1.83 |
| 33 | 1.86 |
| 34 | 2.05 |
| 35 | 2.47 |
| 36 | 2.94 |
| 37 | 3.43 |
| 38 | 3.93 |
| 39 | 4.32 |
| 40 | 4.69 |
| 41 | 4.94 |
| 42 | 5.27 |
| 43 | 5.59 |
| 44 | 5.88 |
| 45 | 6.12 |
| 46 | 6.43 |
| 47 | 6.78 |
| 48 | 7.08 |
| 49 | 7.35 |
| 50 | 7.67 |
| 51 | 7.92 |
| 52 | 8.21 |
| 53 | 8.54 |
| 54 | 8.86 |
| 55 | 9.11 |

| Cycle | Signal |
|---|---|
| 56 | 9.36 |
| 57 | 9.65 |
| 58 | 9.89 |
| 59 | 10.15 |
| 60 | 10.44 |

FIG. 12a

FIG. 12b: Raw Data
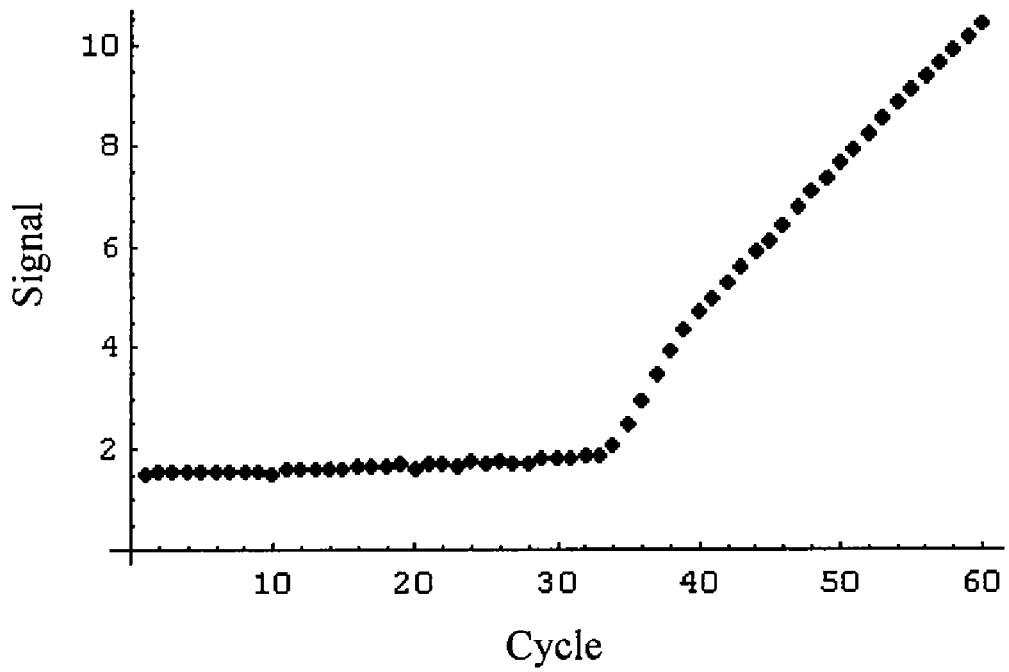
FIG. 13: Raw Data and Double Sigmoid Fit
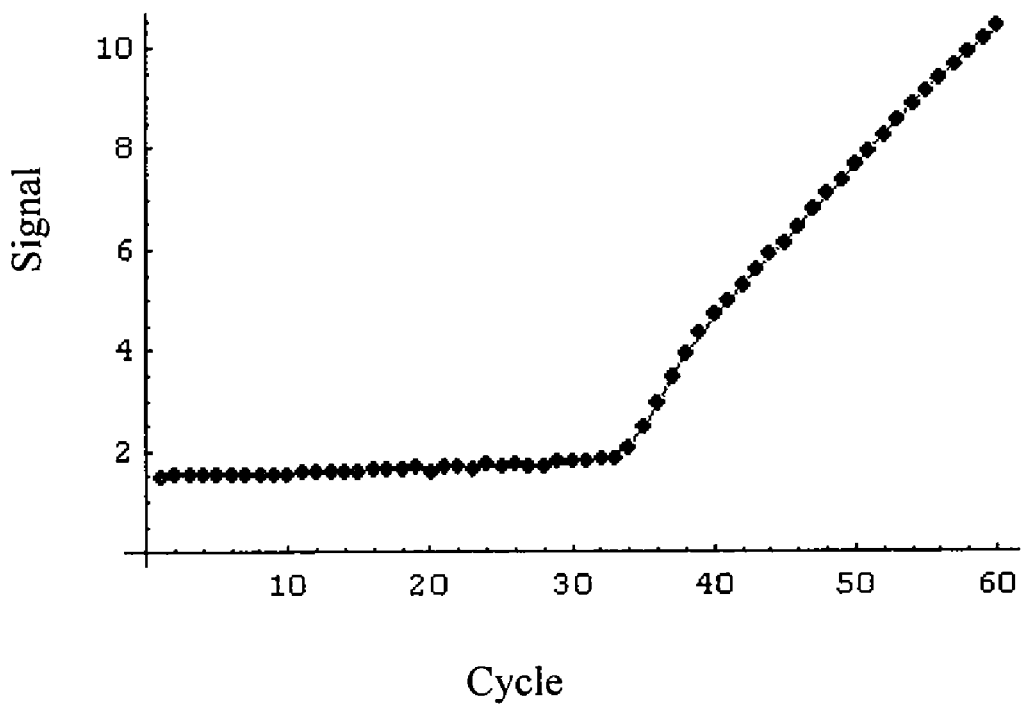

FIG. 14: Normalized Data and Double Sigmoid Fit
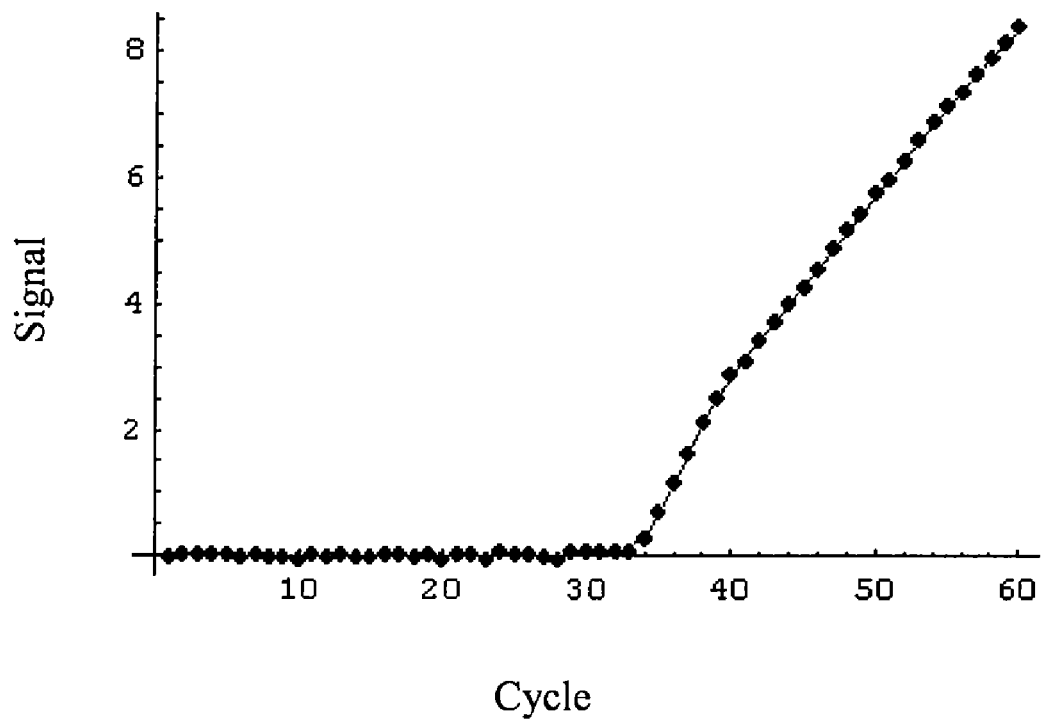
FIG. 15: Curvature Plot
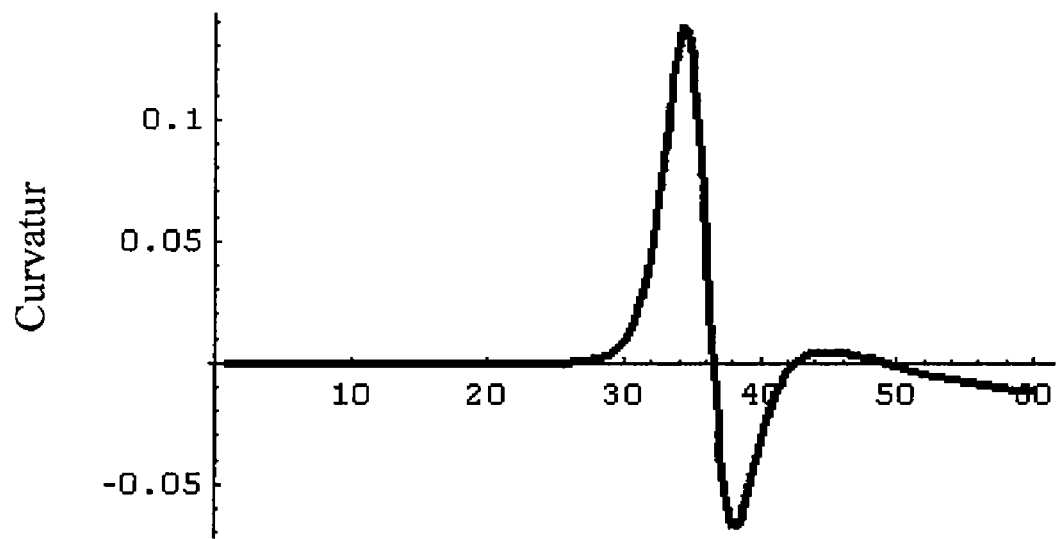

FIG. 16: Radius of Curvature
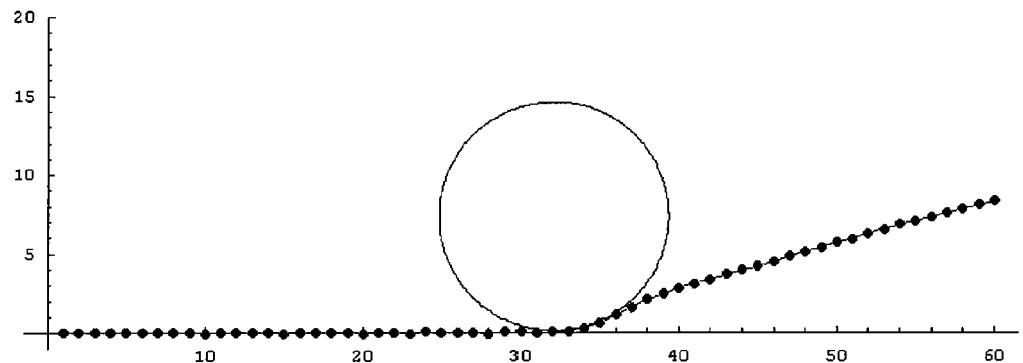
FIG. 17: Raw Data
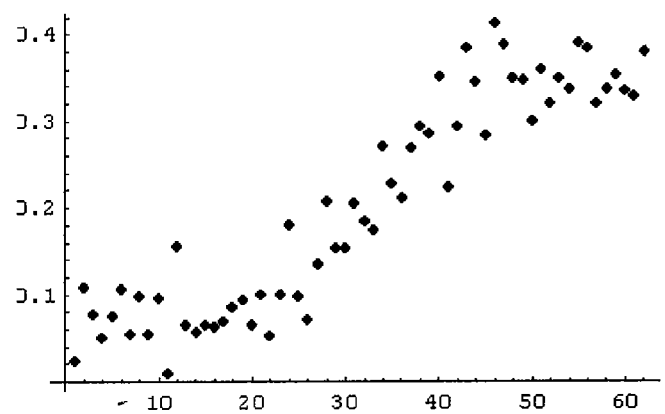
FIG. 18: Baseline Subtraction and Double Sigmoid
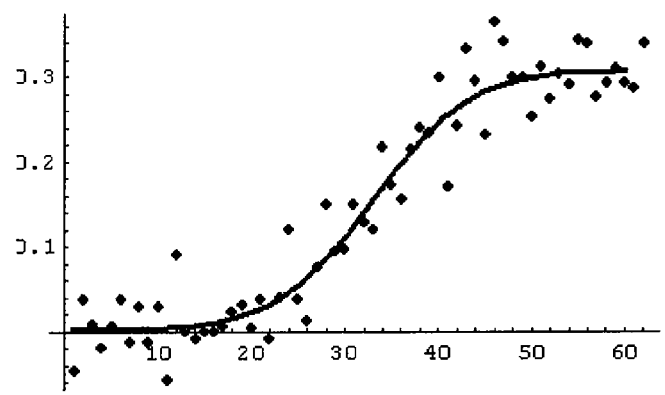

FIG. 19: Curvature Plot
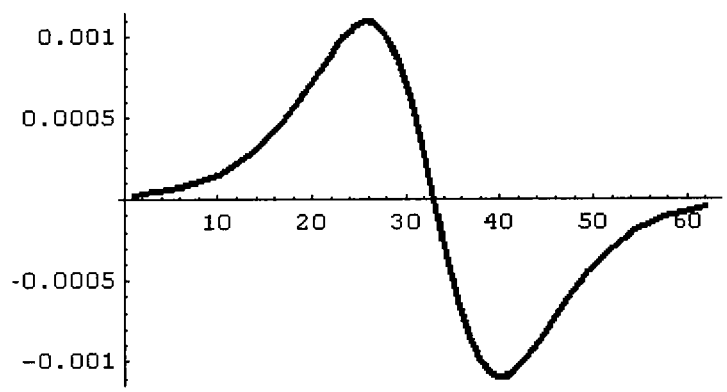
FIG. 20: Raw Data Set
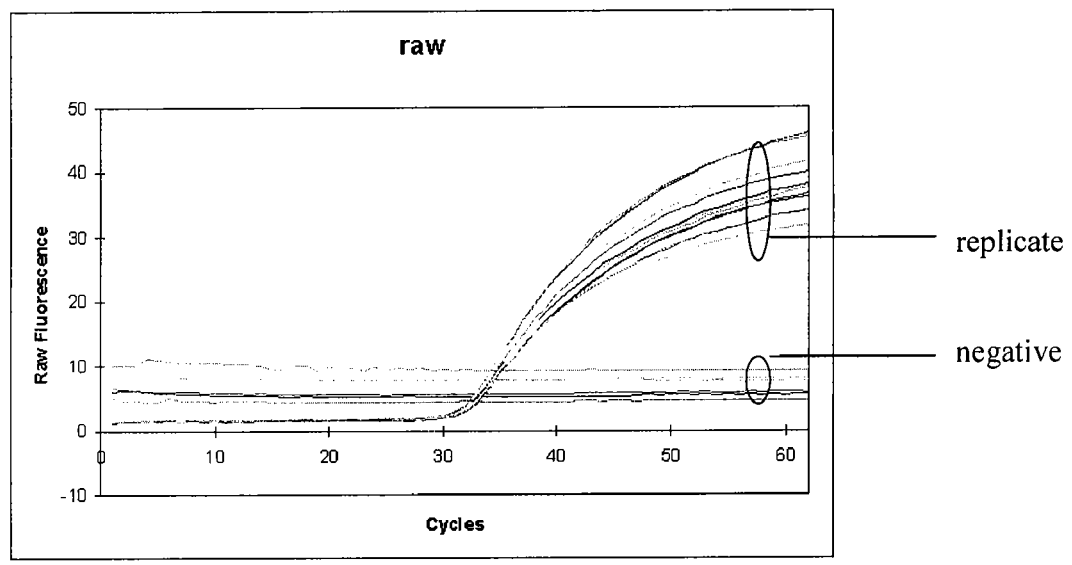

PCR ELBOW DETERMINATION USING CURVATURE ANALYSIS OF A DOUBLE SIGMOID

CROSS-REFERENCES TO RELATED APPLICATIONS

This application is a continuation-in-part (CIP) of the U.S. application Ser. No. 11/316,315, filed Dec. 20, 2005, titled "Levenberg-Marquardt Outlier Spike Removal Method," which is hereby incorporated by reference in its entirety.

BACKGROUND OF THE INVENTION

The present invention relates generally to systems and methods for processing data representing sigmoid or growth curves, and more particularly to systems and methods for determining characteristic cycle threshold (Ct) or elbow values in PCR amplification curves, or elbow values in other growth curves.

The Polymerase Chain Reaction (PCR) is an in vitro method for enzymatically synthesizing or amplifying defined nucleic acid sequences. The reaction typically uses two oligonucleotide primers that hybridize to opposite strands and flank a template or target DNA sequence that is to be amplified. Elongation of the primers is catalyzed by a heat-stable DNA polymerase. A repetitive series of cycles involving template denaturation, primer annealing, and extension of the annealed primers by the polymerase results in an exponential accumulation of a specific DNA fragment. Fluorescent probes or markers are typically used in the process to facilitate detection and quantification of the amplification process.

A typical real-time PCR curve is shown in FIG. 1, where fluorescence intensity values are plotted vs. cycle number for a typical PCR process. In this case, the formation of PCR products is monitored in each cycle of the PCR process. The amplification is usually measured in thermocyclers which include components and devices for measuring fluorescence signals during the amplification reaction. An example of such a thermocycler is the Roche Diagnostics LightCycler (Cat. No. 20110468). The amplification products are, for example, detected by means of fluorescent labelled hybridization probes which only emit fluorescence signals when they are bound to the target nucleic acid or in certain cases also by means of fluorescent dyes that bind to double-stranded DNA.

For a typical PCR curve, identifying a transition point at the end of the baseline region, which is referred to commonly as the elbow value or cycle threshold (Ct) value, is extremely useful for understanding characteristics of the PCR amplification process. The Ct value may be used as a measure of efficiency of the PCR process. For example, typically a defined signal threshold is determined for all reactions to be analyzed and the number of cycles (Ct) required to reach this threshold value is determined for the target nucleic acid as well as for reference nucleic acids such as a standard or housekeeping gene. The absolute or relative copy numbers of the target molecule can be determined on the basis of the Ct values obtained for the target nucleic acid and the reference nucleic acid (Gibson et al., Genome Research 6:995-1001; Bieche et al., Cancer Research 59:2759-2765, 1999; WO 97/46707; WO 97/46712; WO 97/46714). The elbow value in region 20 at the end of the baseline region 15 in FIG. 1 would be in the region of cycle number 30.

The elbow value in a PCR curve can be determined using several existing methods. For example, various current methods determine the actual value of the elbow as the value where the fluorescence reaches a predetermined level called the AFL (arbitrary fluorescence value). Other current methods might use the cycle number where the second derivative of fluorescence vs. cycle number reaches a maximum. All of these methods have drawbacks. For example, some methods are very sensitive to outlier (noisy) data, and the AFL value approach does not work well for data sets with high baselines. Traditional methods to determine the baseline stop (or end of the baseline) for the growth curve shown in FIG. 1 may not work satisfactorily, especially in a high titer situation. Furthermore, these algorithms typically have many parameters (e.g., 50 or more) that are poorly defined, linearly dependent, and often very difficult, if not impossible, to optimize.

Therefore it is desirable to provide systems and methods for determining the elbow value in curves, such as sigmoid-type or growth curves, and PCR curves in particular, which overcome the above and other problems.

BRIEF SUMMARY OF THE INVENTION

The present invention provides novel, efficient systems and methods for determining characteristic transition values such as elbow values in sigmoid or growth-type curves. In one implementation, the systems and methods of the present invention are particularly useful for determining the cycle threshold (Ct) value in PCR amplification curves.

According to the present invention, a double sigmoid function with parameters determined by a Levenberg-Marquardt (LM) regression process is used to find an approximation to a curve that fits a PCR dataset. Once the parameters have been determined, the curve can be normalized using one or more of the determined parameters. After normalization, the normalized curve is processed to determine the curvature of the curve at some or all points along the curve, e.g., to produce a dataset or plot representing the curvature v. the cycle number. The cycle number at which the maximum curvature occurs corresponds to the Ct value. The Ct value is then returned and may be displayed or otherwise used for further processing.

According to one aspect of the present invention, a computer implemented method of determining a point at the end of the baseline region of a growth curve is provided. The method typically includes the steps of receiving a dataset representing a growth curve, the dataset including a plurality of data points each having a pair of coordinate values, and calculating an approximation of a curve that fits the dataset by applying a Levenberg-Marquardt (LM) regression process to a double sigmoid function to determine parameters of the function. The method further typically includes normalizing the curve using the determined parameters to produce a normalized curve, and processing the normalized curve to determine a coordinate value of a point of maximum curvature, wherein the point represents the end of the baseline region of the growth curve. In one aspect, the normalized curve is processed to determine the curvature at some or all points along the curve. In one aspect, the curve is an amplification curve for a kinetic Polymerase Chain Reaction (PCR) process, and the point at the end of the baseline region represents the elbow or cycle threshold (Ct) value for the kinetic PCR curve, wherein the point with maximum curvature represents the Ct value. In certain aspects, normalizing includes subtracting off a linear growth portion of the curve. In certain aspects, a received dataset includes a dataset that has been processed to remove one or more outliers or spike points.

According to another aspect of the present invention, a computer-readable medium including code for controlling a processor to determine a point at the end of the baseline region of a growth curve is provided. The code typically includes instructions to receive a dataset representing a growth curve, the dataset including a plurality of data points each having a pair of coordinate values, and calculate an approximation of a curve that fits the dataset by applying a Levenberg-Marquardt (LM) regression process to a double sigmoid function to determine parameters of the function. The code also typically includes instructions to normalize the curve using the determined parameters to produce a normalized curve, and process the normalized curve to determine a coordinate value of a point of maximum curvature, wherein the point represents the end of the baseline region of the growth curve. In one aspect, the normalized curve is processed to determine the curvature at some or all points along the curve. In one aspect, the curve is an amplification curve for a kinetic Polymerase Chain Reaction (PCR) process, and the point at the end of the baseline region represents the elbow or cycle threshold (Ct) value for the kinetic PCR curve, wherein the point with maximum curvature represents the Ct value. In certain aspects, normalizing includes subtracting off a linear growth portion of the curve.

According to yet another aspect of the present invention, a kinetic Polymerase Chain Reaction (PCR) system is provided. The system typically includes a kinetic PCR analysis module that generates a PCR dataset representing a kinetic PCR amplification curve, the dataset including a plurality of data points, each having a pair of coordinate values, wherein the dataset includes data points in a region of interest which includes a cycle threshold (Ct) value, and an intelligence module adapted to process the PCR dataset to determine the Ct value. The intelligence module typically processes the PCR dataset by calculating an approximation of a curve that fits the dataset by applying a Levenberg-Marquardt (LM) regression process to a double sigmoid function to determine parameters of the function, by normalizing the curve using the determined parameters to produce a normalized curve, and by processing the normalized curve to determine a coordinate value of a point of maximum curvature, wherein the point represents the cycle threshold (Ct) value of the growth curve. In one aspect, the normalized curve is processed to determine the curvature at some or all points along the curve, wherein the point with maximum curvature represents the Ct value.

In certain aspects, the double sigmoid function is of the form:

$$a + bx + \frac{c}{(1 + \exp^{-d(x-e)})(1 + \exp^{-f(x-g)})},$$

wherein calculating includes iteratively determining one or more of the parameters a, b, c, d, e, f and g of the function. In certain aspects, the curve fit is normalized by subtracting off the linear growth portion, a+bx, from the curve.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 1 illustrates an example of a typical PCR growth curve, plotted as fluorescence intensity vs. cycle number.

FIG. 2 shows a process flow for determining the end of a baseline region of a growth curve, or Ct value of a PCR curve.

FIG. 4 illustrates a decomposition of the double sigmoid equation including parameters (a)-(g).

FIG. 5 shows the influence of parameter (d) on the curve and the position of (e), the x value of the inflexion point. All curves in FIG. 5 have the same parameter values except for parameter (d).

FIG. 6 shows an example of the three curve shapes for the different parameter sets.

FIG. 10a shows a typical growth curve that was fit to experimental data using a double sigmoid, and FIG. 10b shows a plot of a the curvature of the double sigmoid curve of FIG. 10a.

FIG. 11 shows a circle superimposed in the growth curve in FIG. 10a tangential to the point of maximum curvature.

FIG. 12a shows an example of a data set for a growth curve.

FIG. 12b shows a plot of the data set of FIG. 12a.

FIG. 13 shows a double sigmoid fit to the data set of FIG. 12.

FIG. 14 shows the data set (and double sigmoid fit) of FIG. 12 (FIG. 13) after normalization using the baseline subtraction method of equation (6).

FIG. 15 shows a plot of the curvature vs. cycle number for the normalized data set of FIG. 14.

FIG. 16 shows a superposition of a circle with the maximum radius of curvature and the normalized data set of FIG. 14.

FIG. 17 shows an example of a "slow-grower" data set.

FIG. 18 shows the data set of FIG. 17 and a double sigmoid fit after normalization using the baseline subtraction method of equation (6).

FIG. 19 shows a plot of the curvature vs. cycle number for the normalized data set of FIG. 18.

FIG. 20 shows a plot of a set of PCR growth curves, including replicate runs and negative samples.

DETAILED DESCRIPTION OF THE INVENTION

Figure 3:
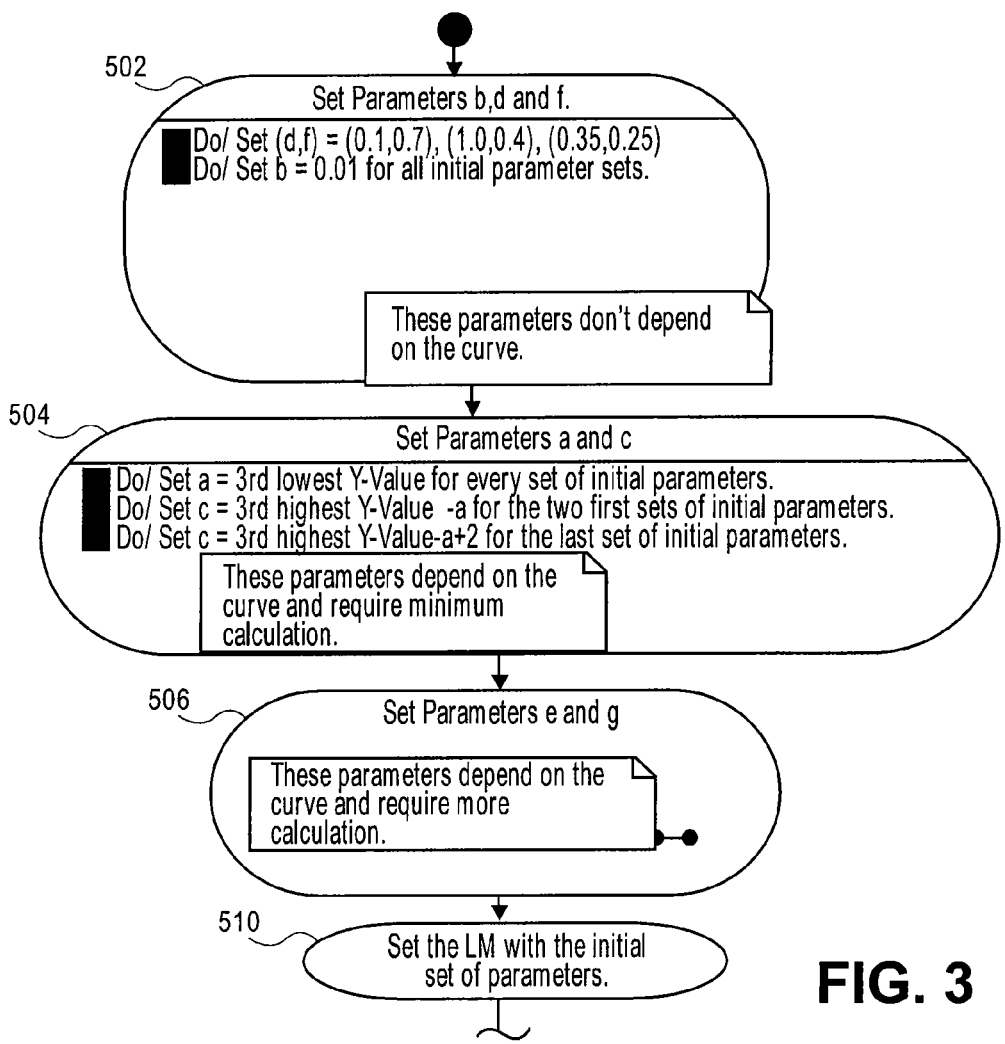
FIG. 3 illustrates a detailed process flow for a spike identification and replacement process according to one embodiment of the present invention.
Figure 3:
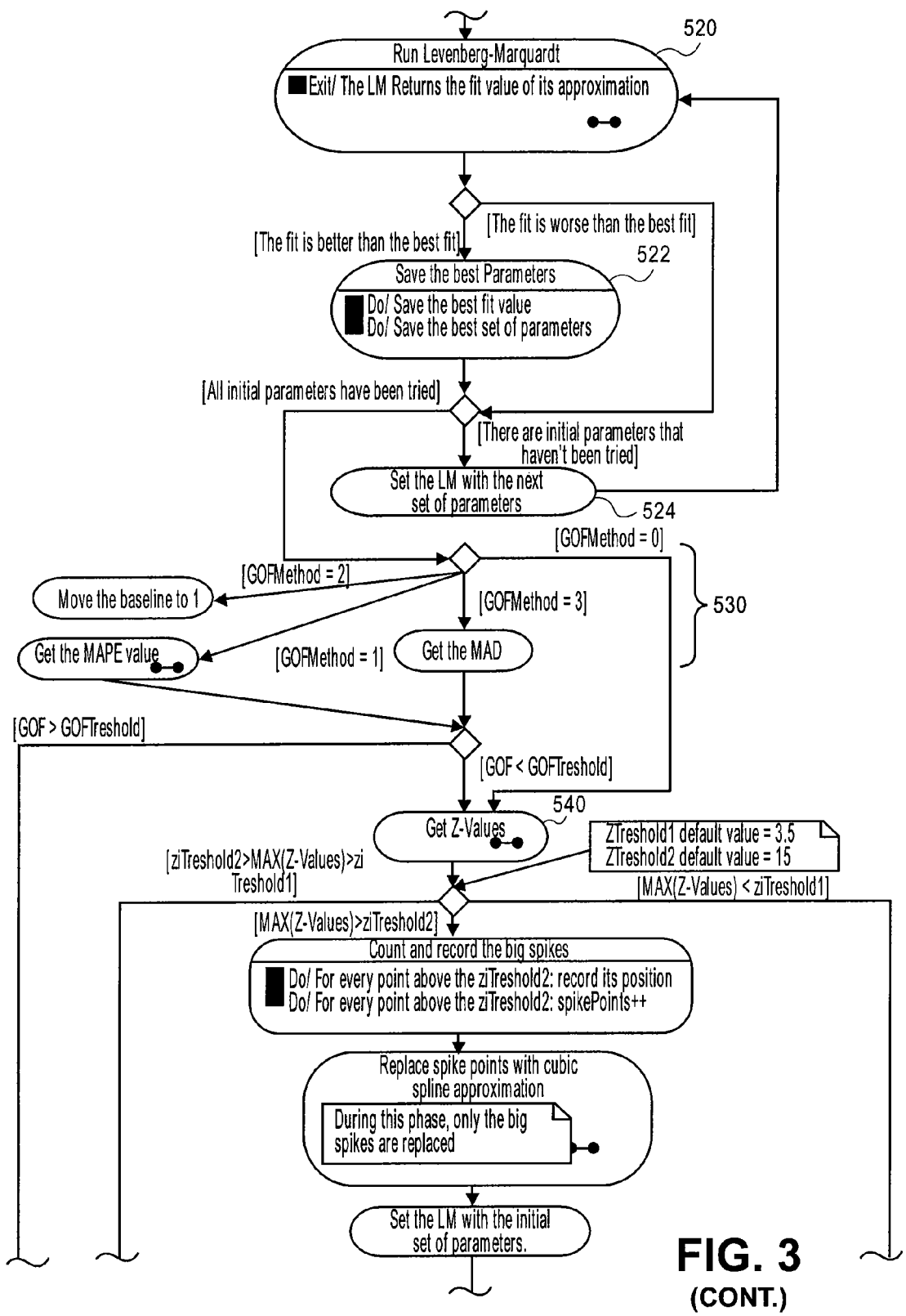
Figure 3:
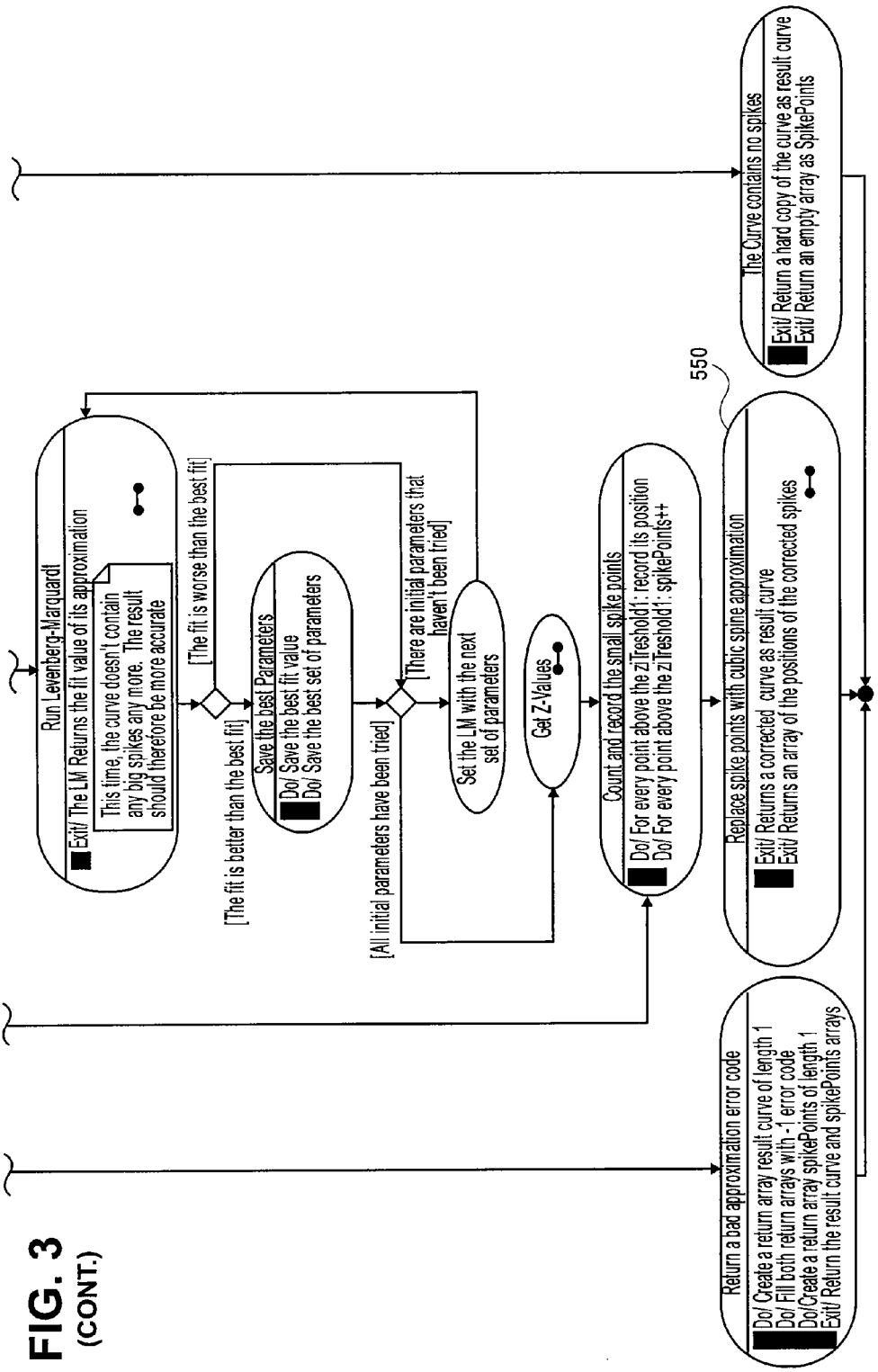

The present invention provides systems and methods for determining a transition value in a sigmoid or growth curve, such as the end of the baseline region or the elbow value or Ct value of a PCR amplification curve. In certain aspects, a double sigmoid function with parameters determined by a Levenberg-Marquardt (LM) regression process is used to find an approximation to the curve. Once the parameters have been determined, the curve can be normalized using one or more of the determined parameters. After normalization, the normalized curve is processed to determine the curvature of the curve at some or all points along the curve, e.g., to produce a dataset or plot representing the curvature v. the cycle number. The cycle number at which the maximum curvature occurs corresponds to the Ct value. The Ct value is then returned and may be displayed or otherwise used for further processing.

One example of a growth or amplification curve 10 in the context of a PCR process is shown in FIG. 1. As shown, the curve 10 includes a lag phase region 15, and an exponential phase region 25. Lag phase region 15 is commonly referred to as the baseline or baseline region. Such a curve 10 includes a transitionary region of interest 20 linking the lag phase and the exponential phase regions. Region 20 is commonly referred to as the elbow or elbow region. The elbow region typically defines an end to the baseline and a transition in the growth or amplification rate of the underlying process. Identifying a specific transition point in region 20 can be useful for analyzing the behavior of the underlying process. In a typical PCR curve, identifying a transition point referred to as the elbow value or cycle threshold (Ct) value is useful for understanding efficiency characteristics of the PCR process.

Other processes that may provide similar sigmoid or growth curves include bacterial processes, enzymatic processes and binding processes. In bacterial growth curves, for example, the transition point of interest has been referred to as the time in lag phase, θ. Other specific processes that produce data curves that may be analyzed according to the present invention include strand displacement amplification (SDA) processes, nucleic acid sequence-based amplification (NASBA) processes and transcription mediated amplification (TMA) processes. Examples of SDA and NASBA processes and data curves can be found in Wang, Sha-Sha, et al., "Homogeneous Real-Time Detection of Single-Nucleotide Polymorphisms by Strand Displacement Amp lification on the BD ProbeTec ET System", Clin Chem 2003 49(10):1599, and Weusten, Jos J. A. M., et al., "Principles of Quantitation of Viral Loads Using Nucleic Acid Sequence-Based Amplification in Combination With Homogeneous Detection Using Molecular Beacons", Nucleic Acids Research, 2002 30(6): 26, respectively, both of which are hereby incorporated by reference. Thus, although the remainder of this document will discuss embodiments and aspects of the invention in terms of its applicability to PCR curves, it should be appreciated that the present invention may be applied to data curves related to other processes.

As shown in FIG. 1, data for a typical PCR growth curve can be represented in a two-dimensional coordinate system, for example, with PCR cycle number defining the x-axis and an indicator of accumulated polynucleotide growth defining the y-axis. Typically, as shown in FIG. 1, the indicator of accumulated growth is a fluorescence intensity value as the use of fluorescent markers is perhaps the most widely used labeling scheme. However, it should be understood that other indicators may be used depending on the particular labeling and/or detection scheme used. Examples of other useful indicators of accumulated signal growth include luminescence intensity, chemiluminescence intensity, bioluminescence intensity, phosphorescence intensity, charge transfer, voltage, current, power, energy, temperature, viscosity, light scatter, radioactive intensity, reflectivity, transmittance and absorbance. The definition of cycle can also include time, process cycles, unit operation cycles and reproductive cycles.

General Process Overview

According to the present invention, one embodiment of a process 100 for determining a transitionary value in a single sigmoid curve, such as the elbow value or Ct value of a kinetic PCR amplification curve, can be described briefly with reference to FIG. 2. In step 110, an experimental data set representing the curve is received or otherwise acquired. An example of a plotted PCR data set is shown in FIG. 1, where the y-axis and x-axis represent fluorescence intensity and cycle number, respectively, for a PCR curve. In certain aspects, the data set should include data that is continuous and equally spaced along an axis.

In the case where process 100 is implemented in an intelligence module (e.g., processor executing instructions) resident in a PCR data acquiring device such as a thermocycler, the data set may be provided to the intelligence module in real time as the data is being collected, or it may be stored in a memory unit or buffer and provided to the intelligence module after the experiment has been completed. Similarly, the data set may be provided to a separate system such as a desktop computer system or other computer system, via a network connection (e.g., LAN, VPN, intranet, Internet, etc.) or direct connection (e.g., USB or other direct wired or wireless connection) to the acquiring device, or provided on a portable medium such as a CD, DVD, floppy disk or the like. In certain aspects, the data set includes data points having a pair of coordinate values (or a 2-dimensional vector). For PCR data, the pair of coordinate values typically represents the cycle number and the fluorescence intensity value. After the data set has been received or acquired in step 110, the data set may be analyzed to determine the end of the baseline region.

In step 120, an approximation of the curve is calculated. During this step, in one embodiment, a double sigmoid function with parameters determined by a Levenberg-Marquardt (LM) regression process or other regression process is used to find an approximation of a curve representing the data set. The approximation is said to be "robust" as outlier or spike points have a minimal effect on the quality of the curve fit. FIG. 13, which will be discussed below, illustrates an example of a plot of a received data set and a robust approximation of the data set determined by using a Levenberg-Marquardt regression process to determine the parameters of a double sigmoid function according to the present invention.

In certain aspects, outlier or spike points in the dataset are removed or replaced prior to processing the data set to determine the end of the baseline region. Spike removal may occur before or after the dataset is acquired in step 110. FIG. 3 illustrates the process flow for identifying and replacing spike points in datasets representing PCR or other growth curves. A more detailed description of a process for determining and removing or replacing spike points can be found in U.S. patent application Ser. No. 11/316,315, titled "Levenberg Marquardt Outlier Spike Removal Method," filed on Dec. 20, 2005, the disclosure of which is incorporated by reference in its entirety.

In step 130, the parameters determined in step 120 are used to normalize the curve, e.g., to remove the baseline slope, as will be described in more detail below. Normalization in this manner allows for determining the Ct value without having to determine or specify the end of the baseline region of the curve or a baseline stop position. In step 140, the normalized curve is then processed to determine the Ct value as will be discussed in more detail below.

LM Regression Process

Steps 502 through 524 of FIG. 3, as will be discussed below, illustrate a process flow for approximating the curve of a dataset and determining the parameters of a fit function (step 120). These parameters can be used in normalizing the curve, e.g., modifying or removing the baseline slope of the data set representing a sigmoid or growth type curve such as a PCR curve according to one embodiment of the present invention (step 130). Where the dataset has been processed to produce a modified dataset with removed or replaced spike points, the modified spikeless dataset may be processed according to steps 502 through 524 to identify the parameters of the fit function.

In one embodiment as shown, a Levenberg-Marquardt (LM) method is used to calculate a robust curve approximation of a data set. The LM method is a non-linear regression process; it is an iterative technique that minimizes the distance between a non-linear function and a data set. The process behaves like a combination of a steepest descent process and a Gauss-Newton process: when the current approximation doesn't fit well it behaves like the steepest descent process (slower but more reliable convergence), but as the current approximation becomes more accurate it will then behave like the Gauss-Newton process (faster but less reliable convergence). The LM regression method is widely used to solve non-linear regression problems.

In general, the LM regression method includes an algorithm that requires various inputs and provides output. In one aspect, the inputs include a data set to be processed, a function that is used to fit the data, and an initial guess for the parameters or variables of the function. The output includes a set of parameters for the function that minimizes the distance between the function and the data set.

According to one embodiment, the fit function is a double sigmoid of the form:

$$f(x) = a + bx + \frac{c}{(1 + \exp^{-d(x-e)})(1 + \exp^{-f(x-g)})}. \quad (1)$$

The choice of this equation as the fit function is based on its flexibility and its ability to fit the different curve shapes that a typical PCR curve or other growth curve may take. One skilled in the art will appreciate that variations of the above fit function or other fit functions may be used as desired.

The double sigmoid equation (1) has 7 parameters: a, b, c, d, e, f and g. The equation can be decomposed into a sum of a constant, a slope and a double sigmoid. The double sigmoid itself is the multiplication of two sigmoids. FIG. 4 illustrates a decomposition of the double sigmoid equation (1). The parameters d, e, f and g determine the shape of the two sigmoids. To show their influence on the final curve, consider the single sigmoid:

$$\frac{1}{1 + \exp^{-d(x-e)}}, \quad (2)$$

where the parameter d determines the "sharpness" of the curve and the parameter e determines the x-value of the inflexion point. FIG. 5 shows the influence of the parameter d on the curve and of the parameter e on the position of the x value of the inflexion point. Table 1, below, describes the influence of the parameters on the double sigmoid curve.

TABLE 1

Double sigmoid parameters description

| Parameter | Influence on the curve |
|---|---|
| a | Value of y at x = 0 |
| b | baseline and plateau slope |
| c | AFI of the curve |
| d | "sharpness" of the first sigmoid (See FIG. 5) |
| e | position of the inflexion point of the first sigmoid (See FIG. 5) |
| f | "sharpness" of the second sigmoid |
| g | position of the inflexion point of the second sigmoid |

In one aspect, the "sharpness" parameters d and f of the double sigmoid equation should be constrained in order to prevent the curve from taking unrealistic shapes. Therefore, in one aspect, any iterations where d<−1 or d>1.1 or where f<−1 or f>1.1 is considered unsuccessful. In other aspects, different constraints on parameters d and f may be used.

Because the Levenberg-Marquardt algorithm is an iterative algorithm, an initial guess for the parameters of the function to fit is typically needed. The better the initial guess, the better the approximation will be and the less likely it is that the algorithm will converge towards a local minimum. Due to the complexity of the double sigmoid function and the various shapes of PCR curves or other growth curves, one initial guess for every parameter may not be sufficient to prevent the algorithm from sometimes converging towards local minima. Therefore, in one aspect, multiple (e.g., three or more) sets of initial parameters are input and the best result is kept. In one aspect, most of the parameters are held constant across the multiple sets of parameters used; only parameters c, d and f may be different for each of the multiple parameter sets. FIG. 6 shows an example of the three curve shapes for the different parameter sets. The choice of these three sets of parameters is indicative of three possible different shapes of curves representing PCR data. It should be understood that more than three sets of parameters may be processed and the best result kept.

As shown in FIG. 3, the initial input parameters of the LM method are identified in step 510. These parameters may be input by an operator or calculated. According to one aspect, the parameters are determined or set according to steps 502, 504 and 506 as discussed below.

Calculation of Initial Parameter (a):

The parameter (a) is the height of the baseline; its value is the same for all sets of initial parameters. In one aspect, in step 504 the parameter (a) is assigned the 3rd lowest y-axis value, e.g., fluorescence value, from the data set. This provides for a robust calculation. In other aspects, of course, the parameter (a) may be assigned any other fluorescence value as desired such as the lowest y-axis value, second lowest value, etc.

Calculation of Initial Parameter (b):

The parameter (b) is the slope of the baseline and plateau. Its value is the same for all sets of initial parameters. In one aspect, in step 502 a static value of 0.01 is assigned to (b) as ideally there shouldn't be any slope. In other aspects, the parameter (b) may be assigned a different value, for example, a value ranging from 0 to about 0.5.

Calculation of Initial Parameter (c):

The parameter (c) represents the height of the plateau minus the height of the baseline, which is denoted as the absolute fluorescence increase, or AFI. In one aspect, for the first set of parameters, c=AFI+2, whereas for the last two parameters, c=AFI. This is shown in FIG. 6, where for the last two sets of parameters, c=AFI. For the first set of parameters, c=AFI+2. This change is due to the shape of the curve modeled by the first set of parameters, which doesn't have a plateau.

Calculation of Parameters (d) and (f):

The parameters (d) and (f) define the sharpness of the two sigmoids. As there is no way of giving an approximation based on the curve for these parameters, in one aspect three static representative values are used in step 502. It should be understood that other static or non-static values may be used for parameters (d) and/or (f). These pairs model the most common shapes on PCR curves encountered. Table 2, below, shows the values of (d) and (f) for the different sets of parameters as shown in FIG. 6.

TABLE 2

Values of parameters d and f

| Parameter set number | Value of d | Value of f |
|---|---|---|
| 1 | 0.1 | 0.7 |
| 2 | 1.0 | 0.4 |
| 3 | 0.35 | 0.25 |

Figure 7:
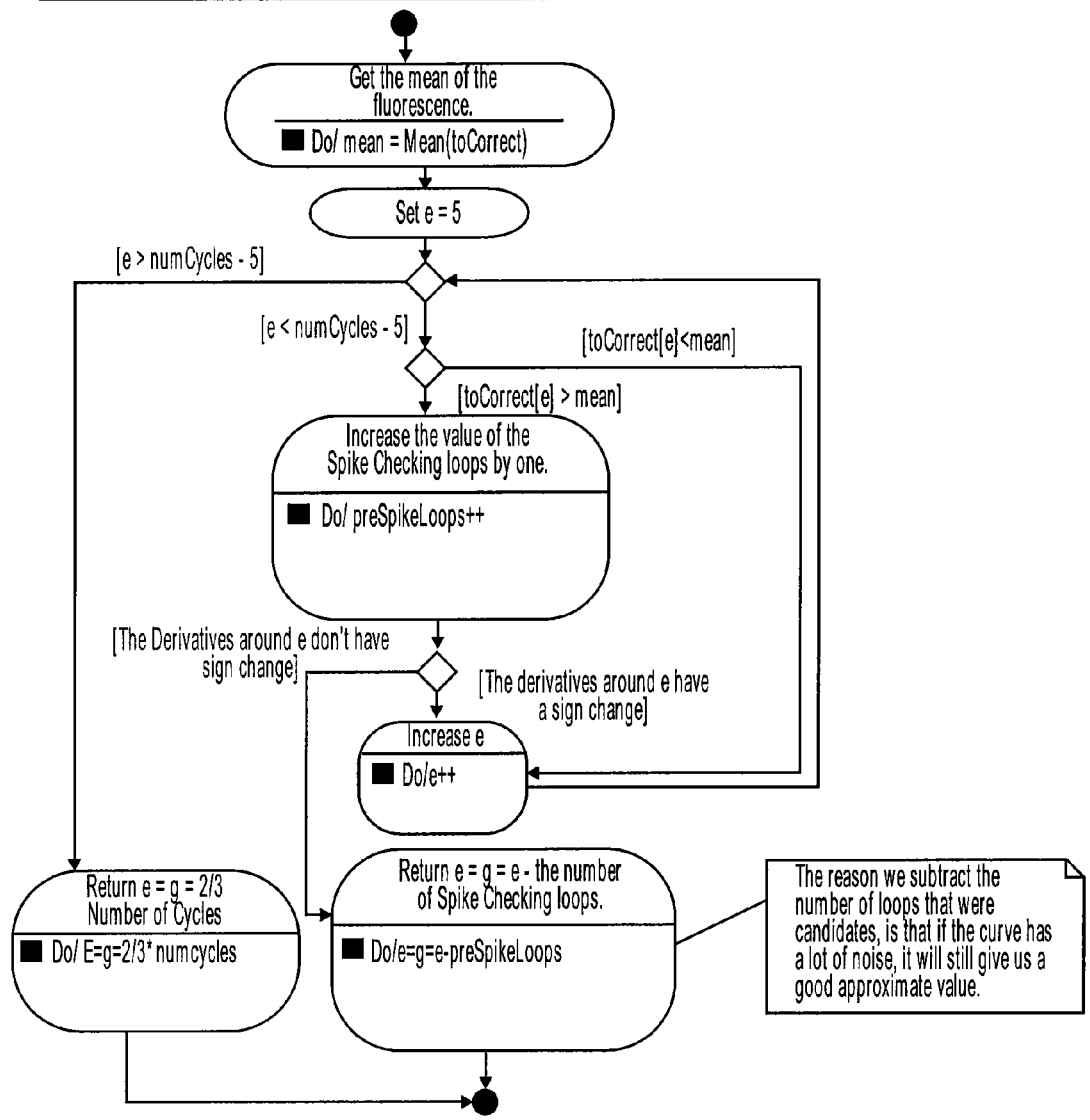
FIG. 7 illustrates a process for determining the value of double sigmoid equation parameters (e) and (g) according to one aspect.

Calculation of Parameters (e) and (g):

In step 506, the parameters (e) and (g) are determined. The parameters (e) and (g) define the inflexion points of the two sigmoids. In one aspect, they both take the same value across all the initial parameter sets. Parameters (e) and (g) may have the same or different values. To find an approximation, in one aspect, the x-value of the first point above the mean of the intensity, e.g., fluorescence, (which isn't a spike) is used. A process for determining the value of (e) and (g) according to this aspect is shown in FIG. 7 and discussed below. A more detailed description of the process for determining the value of the parameters (e) and (g), and other parameters, according to this aspect can be found in U.S. patent application Ser. No. 11/316,315, filed on Dec. 20, 2005, the disclosure of which was previously incorporated by reference in its entirety.

With reference to FIG. 7, initially, the mean of the curve (e.g., fluorescence intensity) is determined. Next, the first data point above the mean is identified. It is then determined whether:

a. that point does not lie near the beginning, e.g., within the first 5 cycles, of the curve;
b. that point does not lie near the end, e.g., within the 5 last cycles, of the curve; and
c. the derivatives around the point (e.g., in a radius of 2 points around it) do not show any change of sign. If they do, the point is likely to be a spike and should therefore be rejected.

Table 3, below, shows examples of initial parameter values as used in FIG. 6 according to one aspect.

TABLE 3

Initial parameters values:

| | Initial parameter set number | | |
|---|---|---|---|
| | 1 | 2 | 3 |
| Value of a | 3$^{rd}$ lowest fluorescence value | 3$^{rd}$ lowest fluorescence value | 3$^{rd}$ lowest fluorescence value |
| Value of b | 0.01 | 0.01 | 0.01 |
| Value of c | 3$^{rd}$ highest fluorescence value - a + 2 | 3$^{rd}$ highest fluorescence value - a | 3$^{rd}$ highest fluorescence value - a |
| Value of d | 0.1 | 1.0 | 0.35 |
| Value of e | X of the first non-spiky point above the mean of the fluorescence | X of the first non-spiky point above the mean of the fluorescence | X of the first non-spiky point above the mean of the fluorescence |
| Value of f | 0.7 | 0.4 | 0.25 |
| Value of g | X of the first non-spiky point above the mean of the fluorescence | X of the first non-spiky point above the mean of the fluorescence | X of the first non-spiky point above the mean of the fluorescence |

Returning to FIG. 3, once all the parameters are set in step 510, a LM process 520 is executed using the input data set, function and parameters. Traditionally, the Levenberg-Marquardt method is used to solve non-linear least-square problems. The traditional LM method calculates a distance measure defined as the sum of the square of the errors between the curve approximation and the data set. However, when minimizing the sum of the squares, it gives outliers an important weight as their distance is larger than the distance of non-spiky data points, often resulting in inappropriate curves or less desirable curves. Therefore, according to one aspect of the present invention, the distance between the approximation and the data set is computed by minimizing the sum of absolute errors as this does not give as much weight to the outliers. In this aspect, the distance between the approximation and data is given by:

$$\text{distance} = \sum |y_{data} - y_{approximation}|. \tag{3}$$

As above, in one aspect, each of the multiple (e.g., three) sets of initial parameters are input and processed and the best result is kept as shown in steps 522 and 524, where the best result is the parameter set that provides the smallest or minimum distance in equation (3). In one aspect, most of the parameters are held constant across the multiple sets of parameters; only c, d and f may be different for each set of parameters. It should be understood that any number of initial parameter sets may be used.

Figure 8:
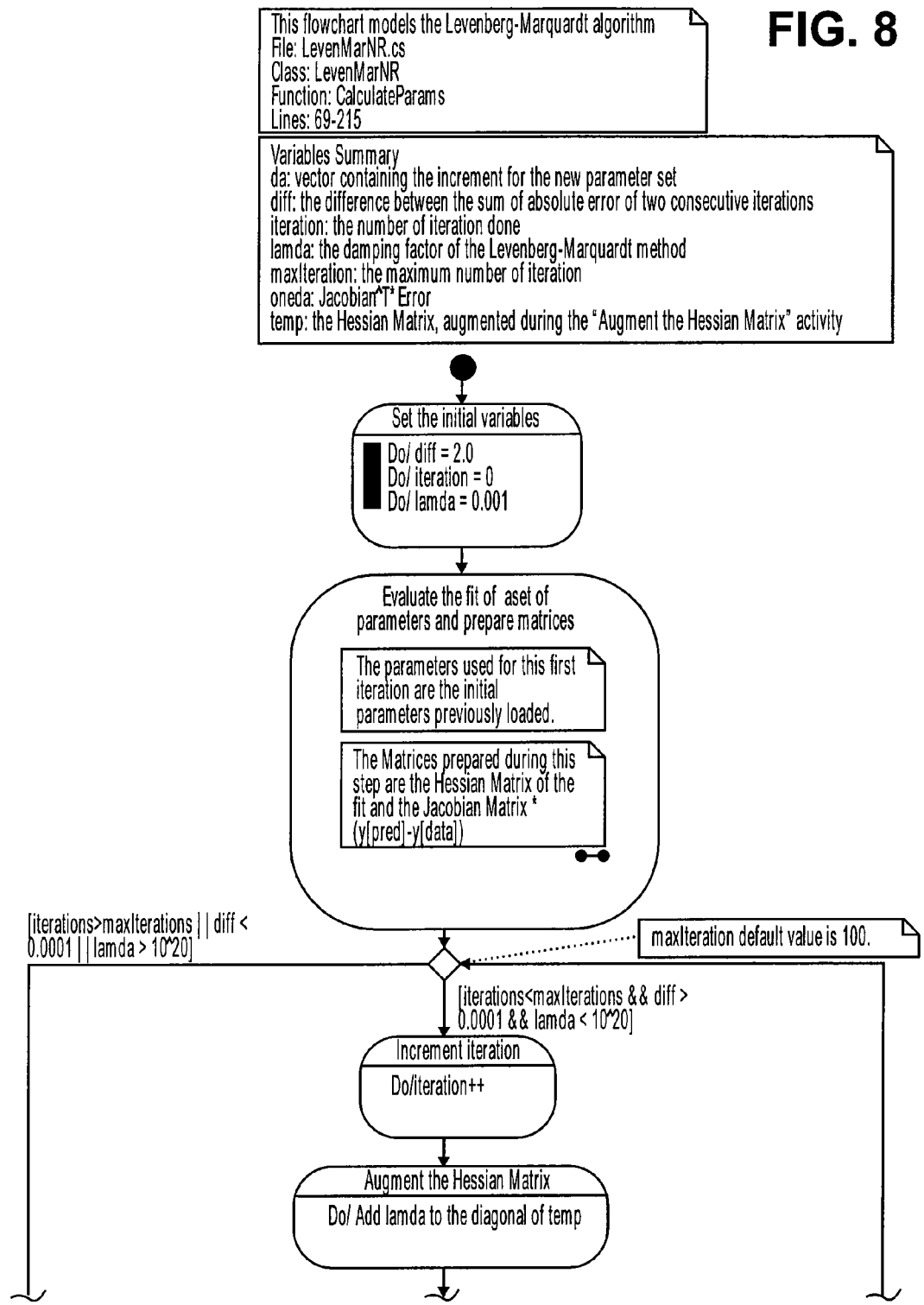
FIG. 8 illustrates a process flow of a Levenberg-Marquardt regression process for an initial set of parameters.
Figure 8:
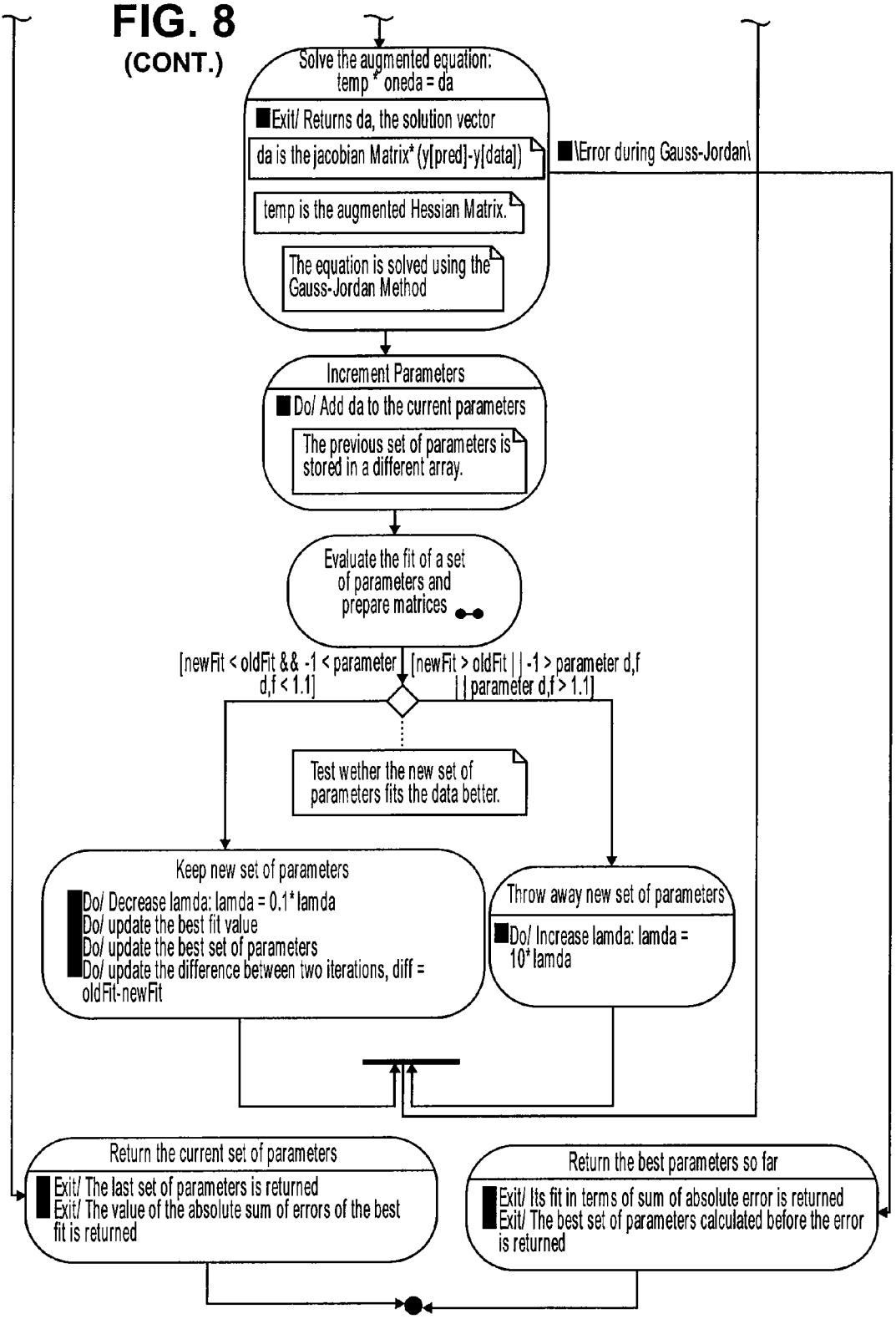

FIG. 8 illustrates a process flow of LM process 520 for a set of parameters according to the present invention. As explained above, the Levenberg-Marquardt method can behave either like a steepest descent process or like a Gauss-Newton process. Its behavior depends on a damping factor $\lambda$. The larger $\lambda$ is, the more the Levenberg-Marquardt algorithm will behave like the steepest descent process. On the other hand, the smaller $\lambda$ is, the more the Levenberg-Marquardt algorithm will behave like the Gauss-Newton process. In one aspect, $\lambda$ is initiated at 0.001. It should be appreciated that $\lambda$ may be initiated at any other value, such as from about 0.000001 to about 1.0.

As stated before, the Levenberg-Marquardt method is an iterative technique. According to one aspect, as shown in FIG. 8 the following is done during each iteration:

1. The Hessian Matrix (H) of the precedent approximation is calculated.
2. The transposed Jacobian Matrix ($J^T$) of the precedent approximation is calculated.
3. The distance vector (d) of the precedent approximation is calculated.
4. The Hessian Matrix diagonal is augmented by the current damping factor $\lambda$:

$$H_{aug} = H\lambda \tag{4}$$

5. Solve the augmented equation:

$$H_{aug}x = J^T d \tag{5}$$

6. The solution x of the augmented equation is added to the parameters of the function.
7. Calculate the distance between the new approximation and the curve.
8. If the distance with this new set of parameters is smaller than the distance with the previous set of parameters:
   The iteration is considered successful.
   Keep or store the new set of parameters.
   Decrease the damping factor $\lambda$, e.g., by a factor 10.
   If the distance with this new set of parameters is larger than the distance with the previous set of parameters:
   The iteration is considered unsuccessful.
   Throw away the new set of parameters.
   Increase the damping factor $\lambda$, e.g., by a factor of 10.

In one aspect, the LM process of FIG. 8 iterates until one of the following criteria is achieved:
1. It has run for a specified number, N, of iterations. This first criterion prevents the algorithm from iterating indefinitely. For example, in one aspect as shown in FIG. 10, the default iteration value N is 100. 100 iterations should be plenty for the algorithm to converge if it can converge. In general, N can range from fewer than 10 to 100 or more.
2. The difference of the distances between two successful iterations is smaller than a threshold value. e.g., 0.0001. When the difference becomes very small, the desired precision has been achieved and continuing to iterate is pointless as the solution won't become significantly better.
3. The damping factor $\lambda$ exceeds a specified value, e.g., is larger than $10^{20}$. When $\lambda$ becomes very large, the algorithm won't converge any better than the current solution, therefore it is pointless to continue iterating. In general, the specified value can be significantly smaller or larger than $10^{20}$.

Normalization

After the parameters have been determined, in one embodiment, the curve is normalized (step 130) using one or more of the determined parameters. For example, in one aspect, the curve may be normalized or adjusted to have zero baseline slope by subtracting out the linear growth portion of the curve. Mathematically, this is shown as:

$$\text{dataNew}(BLS) = \text{data} - (a + bx), \quad (6)$$

where dataNew(BLS) is the normalized signal after baseline subtraction, e.g., the data set (data) with the linear growth or baseline slope subtracted off or removed. The values of parameters a and b are those values determined by using the LM equation to regress the curve, and x is the cycle number. Thus, for every data value along the x-axis, the constant a and the slope b times the x value is subtracted from the data to produce a data curve with a zero baseline slope. In certain aspects, spike points are removed from the dataset prior to applying the LM regression process to the dataset to determine normalization parameters.

In another aspect, the curve may be normalized or adjusted to have zero slope according to the following equation:

$$\text{dataNew}(BLSD) = (\text{data} - (a + bx))/a, \quad (7a)$$

where dataNew(BLSD) is the normalized signal after baseline subtraction with division, e.g., the data set (data) with the linear growth or baseline slope subtracted off or removed and the result divided by a. The value of parameters a and b are those values determined by using the LM equation to regress the curve, and x is the cycle number. Thus, for every data value along the x-axis, the constant a and the slope b times the x value is subtracted from the data and the result divided by the value of parameter a to produce a data curve with a zero baseline slope. In one aspect, equation (7a) is valid for parameter "a"$\geq 1$; in the case where parameter "a"$<1$, then the following equation is used:

$$\text{dataNew}(BLSD) = \text{data} - (a + bx). \quad (7b)$$

In certain aspects, spike points are removed from the dataset prior to applying the LM regression process to the dataset to determine normalization parameters.

In yet another aspect, the curve may be normalized or adjusted according to following equation:

$$\text{dataNew}(BLD) = \text{data}/a, \quad (8a)$$

where dataNew(BLD) is the normalized signal after baseline division, e.g., the data set (data) divided by parameter a. The values are the parameters a and b are those values determined by using the LM equation to regress to curve, and x is the cycle number. In one aspect, equation (8a) is valid for parameter "a"$\geq 1$; in the case where parameter "a"$<1$, then the following equation is used:

$$\text{dataNew}(BLD) = \text{data} + (1 - a). \quad (8b)$$

In certain aspects, spike points are removed from the dataset prior to applying the LM regression process to the dataset to determine normalization parameters.

In yet another aspect, the curve may be normalized or adjusted according to following equation:

$$\text{dataNew}(PGT) = (\text{data} - (a + bx))/c, \quad (9a)$$

where dataNew(PGT) is the normalized signal after baseline subtraction with division, e.g., the data set (data) with the linear growth or baseline slope subtracted off or removed and the result divided by c. The value of parameters a, b and c are those values determined by using the LM equation to regress the curve, and x is the cycle number. Thus, for every data value along the x-axis, the constant a and the slope b times the x value is subtracted from the data and the result divided by the value of parameter c to produce a data curve with a zero baseline slope. In one aspect, equation (9a) is valid for parameter "c"$\geq 1$; in the case where parameter "c"$<1$ and "c"$\geq 0$, then the following equation is used:

$$\text{dataNew}(PGT) = \text{data} - (a + bx). \quad (9b)$$

In certain aspects, spike points are removed from the dataset prior to applying the LM regression process to the dataset to determine normalization parameters.

One skilled in the art will appreciate that other normalization equations may be used to normalized and/or modify the baseline using the parameters as determined by the Levenberg-Marquardt or other regression process.

Curvature Determination

Figure 9:
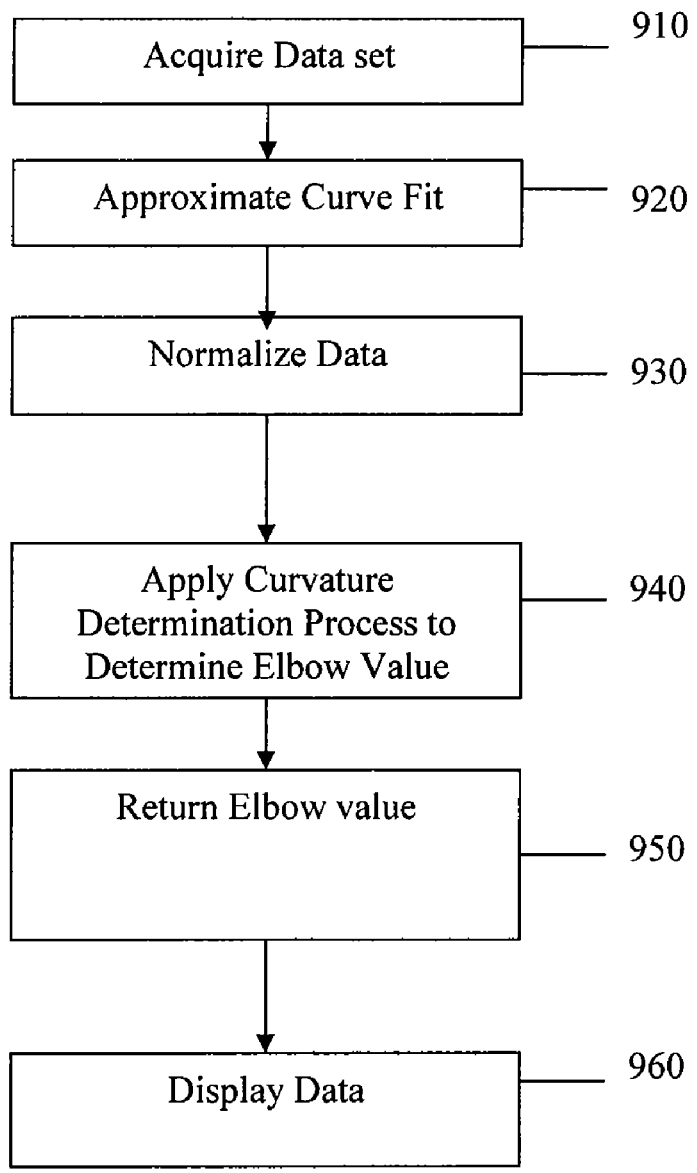
FIG. 9 illustrates a more detailed process flow for determining the elbow value for a PCR process according to one embodiment.

After the curve has been normalized using one of equations (6), (7), (8) or (9), or other normalization equation, the Ct value can be determined. In one embodiment, a curvature determination process or method is applied to the normalized curve as will be described with reference to FIG. 9, which shows a process flow for determining the elbow value or Ct value in a kinetic PCR curve. In step 910, the data set is acquired. In the case where the determination process is implemented in an intelligence module (e.g., processor executing instructions) resident in a PCR data acquiring device such as a thermocycler, the data set may be provided to the intelligence module in real time as the data is being collected, or it may be stored in a memory unit or buffer and provided to the module after the experiment has been completed. Similarly, the data set may be provided to a separate system such as a desktop computer system via a network connection (e.g., LAN, VPN, intranet, Internet, etc.) or direct connection (e.g., USB or other direct wired or wireless connection) to the acquiring device, or provided on a portable medium such as a CD, DVD, floppy disk or the like.

After a data set has been received or acquired, in step 920 an approximation to the curve is determined. During this step, in one embodiment, a double sigmoid function with parameters determined by a Levenberg Marquardt regression process is used to find an approximation of a curve representing the dataset. Additionally, spike points may be removed from the dataset prior to step 920 as described with reference to FIG. 3. For example, the dataset acquired in step 910 can be a dataset with spikes already removed. In step 930, the curve is normalized. In certain aspects, the curve is normalized using one of equations (6), (7), (8) or (9) above. For example, the baseline may be set to zero slope using the parameters of the double sigmoid equation as determined in step with 920 to subtract off the baseline slope as per equation (6) above. In step 940, a process is applied to the normalized curve to determine the curvature at points along the normalized curve. A plot of the curvature v. cycle number may be returned and/or displayed. The point of maximum curvature corresponds to the elbow or Ct value. In step 950, the result is returned, for example to the system that performed the analysis, or to a separate system that requested the analysis. In step 960, Ct value is displayed. Additional data such as the entire data set or the curve approximation may also be displayed. Graphical displays may be rendered with a display device, such as a monitor screen or printer, coupled with the system that performed the analysis of FIG. 9, or data may be provided to a separate system for rendering on a display device.

According to one embodiment, to obtain the Ct value for this curve, the maximum curvature is determined. In one aspect, the curvature is determined for some or all points on the normalized curve. A plot of the curvature vs. cycle number may be displayed. The curvature of a curve is given by the equation, below:

$$kappa(x) = \frac{\left(\frac{d^2 y}{dx^2}\right)}{\left[1+\left(\frac{dy}{dx}\right)^2\right]^{3/2}}. \quad (10)$$

Consider a circle of radius a, given by the equation below:

$$y(x) = \sqrt{a^2 - x^2} \quad (11)$$

The curvature of equation (11) is kappa(x)=−(1/a). Thus, the radius of curvature is equal to the negative inverse of the curvature. Since the radius of a circle is constant, its curvature is given by −(1/a). Now consider FIG. 10b, which is a plot of the curvature of the fit of the PCR data set of FIG. 10a. The Ct value can be considered to occur at the position of maximum curvature, which occurs at cycle number Ct=21.84. This Ct value compares favorably to the PCR growth curve shown in FIG. 10a.

The radius of curvature at the maximum curvature (corresponding to a Ct value of 21.84) is: radius=1/0.2818=3.55 cycles. A circle of this radius superimposed in the PCR growth curve in FIG. 10a is shown in FIG. 11. As FIG. 11 illustrates, a circle of radius corresponding to the maximum curvature represents the largest circle that can be superimposed at the start of the growth region of the PCR curve while remaining tangent to the curve. Curves with a small (maximum) radius of curvature will have steep growth curves while curves with a large (maximum) radius of curvature will have shallow growth curves. If the radius of curvature is extremely large, this is indicative of curves with no apparent signal.

The first and second derivatives of the double sigmoid of equation (1) that are needed in calculating the curvature are shown below.

First Derivative $$\frac{dy}{dx} = b + \frac{ce^{-f(x-g)}f}{(1+e^{-d(x-e)})(1+e^{-f(x-g)})^2} + \frac{cde^{-d(x-e)}}{(1+e^{-d(x-e)})^2(1+e^{-f(x-g)})} \quad (12)$$

Equation (13): Second Derivative $$\frac{d^2 y}{dx^2} = \frac{c\left(\frac{2d^2 e^{-2d(x-e)}}{(1+e^{-d(x-e)})^3} - \frac{d^2 e^{-d(x-e)}}{(1+e^{-d(x-e)})^2}\right)}{1+e^{-f(x-g)}} + \frac{2cde^{-d(x-e)-f(x-g)}f}{(1+e^{-d(x-e)})^2(1+e^{-f(x-g)})^2} + \frac{c\left(\frac{2e^{-2f(x-g)}f^2}{(1+e^{-f(x-g)})^3} - \frac{e^{-f(x-g)}f^2}{(1+e^{-f(x-g)})^2}\right)}{1+e^{-d(x-e)}}$$

EXAMPLES

FIG. 12a shows an example of raw data for a growth curve. Applying the double sigmoid/LM method to the raw data plot shown in FIG. 12b gives values of the seven parameters in equation (1) as shown in Table 4 below:

TABLE 4

| | |
|---|---|
| a | 1.4707 |
| b | 0.0093 |
| c | 10.9421 |
| d | 0.7858 |
| e | 35.9089 |
| f | 0.1081 |
| g | 49.1868 |

The double sigmoid fit to the data shown in FIG. 12 is shown in FIG. 13, indicating a very accurate assessment of the data points. These data were then normalized according to equation (6) (baseline subtraction) to yield the graph shown in FIG. 14. The solid line shown in FIG. 14 is the double sigmoid/LM application of equation (1) to the data set, which has been normalized according to equation (6). FIG. 15 shows a plot of the curvature v. cycle number for the normalized curve of FIG. 14. The maximum in the curvature occurs at cycle number 34.42 at a curvature of 0.1378. Thus, Ct=34.42 based on the cycle number at maximum curvature, and the radius of curvature=1/0.1378=7.25. A superposition of a circle with this radius of curvature and the normalized data set is shown in FIG. 16.

An example of a "slow-grower" data set is shown in FIG. 17. A double sigmoid fit to this data set and normalization using baseline subtraction, equation (6), gives the fit result shown in FIG. 18. The corresponding curvature plot is shown in FIG. 19. The maximum curvature occurs at cycle number 25.90, with a curvature=0.00109274, corresponding to a radius of curvature=915. This large radius of curvature communicates that this is a slow grower data set.

As another example, consider the set of PCR growth curves shown in FIG. 20. A comparison of the Ct values obtained using an existing method ("Threshold") vs. using the curvature method following baseline subtraction with division (BLSD—equation (7)) is shown in Table 5 below.

TABLE 5

| Ct Values | | |
|---|---|---|
| Threshold | Curvature Ct BLSD | ROC BLSD |
| −3.0 | −3.0 | Infinite |
| −1.0 | 21.3 | 2420.0 |
| −1.0 | −3.0 | Infinite |

TABLE 5-continued

Ct Values

| Threshold | Curvature Ct BLSD | ROC BLSD |
|---|---|---|
| −1.0 | 16.6 | 947.5 |
| −1.0 | 31.6 | 1870.2 |
| −1.0 | 10.3 | 1438.8 |
| −1.0 | 28.1 | 6229.8 |
| −1.0 | 19.8 | 3216.3 |
| 29.1 | 31.7 | 6.0 |
| 29.3 | 31.6 | 5.9 |
| 29.4 | 32.0 | 6.5 |
| 29.5 | 31.7 | 6.4 |
| 29.6 | 31.6 | 5.9 |
| 29.6 | 32.1 | 5.9 |
| 29.9 | 32.0 | 6.1 |
| 30.1 | 31.8 | 6.2 |
| 30.1 | 32.0 | 6.1 |
| 30.2 | 31.9 | 6.1 |
| 30.2 | 31.8 | 6.0 |
| 30.2 | 31.8 | 5.7 |
| 30.3 | 31.7 | 5.9 |
| 30.4 | 31.9 | 6.1 |
| 30.6 | 32.1 | 5.9 |
| 30.6 | 32.2 | 6.2 |
| 1.56% | 0.56% | ← Cv |

Table 5 indicates that the Curvature method of calculating Ct values (in this case after normalization with BLSD) gives a smaller Cv (coefficient of variation) than the existing Threshold method. In addition, the radius of curvature (ROC) calculated with the curvature method provides a simple method of differentiating between linear curves and real growth curves.

It should be appreciated that the Ct determination processes, including the curve fitting and curvature determination processes, may be implemented in computer code running on a processor of a computer system. The code includes instructions for controlling a processor to implement various aspects and steps of the Ct determination processes. The code is typically stored on a hard disk, RAM or portable medium such as a CD, DVD, etc. Similarly, the processes may be implemented in a PCR device such as a thermocycler including a processor executing instructions stored in a memory unit coupled to the processor. Code including such instructions may be downloaded to the PCR device memory unit over a network connection or direct connection to a code source or using a portable medium as is well known.

One skilled in the art should appreciate that the elbow determination processes of the present invention can be coded using a variety of programming languages such as C, C++, C#, Fortran, VisualBasic, etc., as well as applications such as Mathematica which provide pre-packaged routines, functions and procedures useful for data visualization and analysis. Another example of the latter is MATLAB®.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A computer-implemented method of determining a point at the end of the baseline region of a growth curve in a kinetic Polymerase Chain Reaction (PCR) amplification curve, comprising the steps, implemented in a computer system having a processor, of:

receiving a dataset representing a growth curve, said dataset including a plurality of data points each having a pair of coordinate values;

calculating an approximation of a curve that fits the dataset by applying a Levenberg-Marquardt (LM) regression process to a double sigmoid function to determine parameters of the function;

normalizing the curve using the determined parameters to produce a normalized curve; and processing the normalized curve to determine a point of maximum curvature, wherein the point of maximum curvature represents the end of the baseline region of the growth curve.

2. The method of claim 1, wherein normalizing includes subtracting off a linear growth portion from the dataset.

3. The method of claim 1, wherein processing includes determining the curvature at some or all points along the normalized curve.

4. The method of claim 3, further including displaying a plot of the curvature of the normalized curve.

5. The method of claim 1, wherein the double sigmoid function is of the form:

$$a + bx + \frac{c}{(1 + \exp^{-d(x-e)})(1 + \exp^{-f(x-g)})},$$

and wherein calculating includes iteratively determining one or more of the parameters a, b, c, d, e, f and g of the function.

6. The method of claim 5, wherein at least the parameters a and b are determined, and wherein normalizing includes subtracting off the linear growth portion, a+bx, from the curve.

7. The method of claim 5, wherein at least the parameter a is determined, and wherein normalizing includes dividing the curve by parameter a.

8. The method of claim 5, wherein at least the parameters a and b are determined, and wherein normalizing includes subtracting off the linear growth portion, a+bx, from the curve and dividing the result by parameter a.

9. The method of claim 5, wherein at least the parameters a, b and c are determined, and wherein normalizing includes subtracting off the linear growth portion, a+bx, from the curve and dividing the result by parameter c.

10. The method of claim 1, wherein the dataset represents a growth curve for a kinetic Polymerase Chain Reaction (PCR) process, and wherein the point at the end of the baseline region represents the elbow or cycle threshold (Ct) of the growth curve.

11. The method of claim 10, wherein the pair of coordinate values represent an accumulation of amplified polynucleotide and a cycle number.

12. The method of claim 10, further including returning the Ct value.

13. The method of claim 10, further including displaying the Ct value.

14. The method of claim 1, wherein the dataset represents a growth curve for a kinetic Polymerase Chain Reaction (PCR) process, a bacterial process, an enzymatic process or a binding process.

15. The method of claim 14, wherein the accumulation of amplified polynucleotide is represented by one of a fluorescence intensity value, a luminescence intensity value, a chemiluminescence intensity value, a phosphorescence intensity value, a charge transfer value, a bioluminescence intensity value, or an absorbance value.

16. A non-transitory computer-readable storage medium including code for controlling a processor to determine a point at the end of the baseline region of a growth curve in a kinetic Polymerase Chain Reaction (PCR) amplification curve, the code including instructions to:
receive a dataset representing a growth curve, said dataset including a plurality of data points each having a pair of coordinate values;
calculate an approximation of a curve that fits the dataset by applying a Levenberg-Marquardt (LM) regression process to a double sigmoid function to determine parameters of the function;
normalize the curve using the determined parameters to produce a normalized curve; and
process the normalized curve to determine a point of maximum curvature, wherein the point of maximum curvature represents the end of the baseline region of the growth curve.

17. The non-transitory computer readable storage medium of claim 16, further including instructions to display the Ct value.

18. The computer readable medium of claim 16, wherein the instructions to normalize include instructions to subtract off a linear growth portion from the dataset.

19. The computer readable medium of claim 16, wherein the instructions to process include instructions to determine the curvature at some or all points along the normalized curve.

20. The computer readable medium of claim 19, further including instructions to display a plot of the curvature of the normalized curve.

21. The computer readable medium of claim 16, wherein the double sigmoid function is of the form:

$$a + bx + \frac{c}{(1 + \exp^{-d(x-e)})(1 + \exp^{-f(x-g)})},$$

and wherein the instruction to calculate include instructions to iteratively determine one or more of the parameters a, b, c, d, e, f and g of the function.

22. The computer readable medium of claim 21, wherein at least the parameters a and b are determined, and wherein the instructions to normalize include instructions to subtract off the linear growth portion, a+bx, from the curve.

23. The computer readable medium of claim 21, wherein at least the parameters a, b and c are determined, and wherein the instructions to normalize include instructions to subtract off the linear growth portion, a+bx, from the curve and divide the result by parameter c.

24. The computer readable medium of claim 21, wherein at least the parameter a is determined, and wherein the instructions to normalize include instructions to divide the curve by parameter a.

25. The computer readable medium of claim 21, wherein at least the parameters a and b are determined, and wherein the instructions to normalize include instructions to subtract off the linear growth portion, a+bx, from the curve and divide the result by parameter a.

26. The computer readable medium of claim 16, wherein the dataset represents a growth curve for a kinetic Polymerase Chain Reaction (PCR) process, a bacterial process, an enzymatic process or a binding process.

27. The computer readable medium of claim 26, further including instructions to return the Ct value.

28. The computer readable medium of claim 16, wherein the dataset represents a growth curve for a kinetic Polymerase Chain Reaction (PCR) process, and wherein the point at the end of the baseline region represents the elbow or cycle threshold (Ct) of the growth curve.

29. The computer readable medium of claim 28, wherein the pair of coordinate values represent an accumulation of amplified polynucleotide and a cycle number.

30. The computer readable medium of claim 29, wherein the accumulation of amplified polynucleotide is represented by one of a fluorescence intensity value, a luminescence intensity value, a chemiluminescence intensity value, a phosphorescence intensity value, a charge transfer value, a bioluminescence intensity value, or an absorbance value.

31. The computer readable medium of claim 16, wherein the code further includes instructions to return or display the coordinate value of the point at the end of the baseline region.

32. A kinetic Polymerase Chain Reaction (PCR) system, comprising:
a kinetic PCR analysis device that generates a PCR dataset representing a kinetic PCR amplification curve, said dataset including a plurality of data points, each having a pair of coordinate values, wherein said dataset includes data points in a region of interest which includes a cycle threshold (Ct) value; and
a processor adapted to process the PCR dataset to determine the Ct value, by:
calculating an approximation of a curve that fits the dataset by applying a Levenberg-Marquardt (LM) regression process to a double sigmoid function to determine parameters of the function;
normalizing the curve using the determined parameters to produce a normalized curve; and
processing the normalized curve to determine a point of maximum curvature, wherein the point of maximum curvature represents the cycle threshold (Ct) value of the growth curve.

33. The system of claim 32, wherein the kinetic PCR analysis device is resident in a kinetic thermocycler device, and wherein the processor is communicably coupled to the analysis device.

34. The system of claim 32, wherein the processor is resident in a computer system coupled to the analysis device by one of a network connection or a direct connection.

35. The system of claim 32, wherein the double sigmoid function is of the form:

$$a + bx + \frac{c}{(1 + \exp^{-d(x-e)})(1 + \exp^{-f(x-g)})},$$

and wherein calculating includes iteratively determining one or more of the parameters a, b, c, d, e, f and g of the function.

36. The system of claim 35, wherein at least the parameters a and b are determined, and wherein normalizing includes subtracting off the linear growth portion, a+bx, from the curve.

37. The system of claim 35, wherein at least the parameters a and b are determined, and wherein normalizing includes subtracting off the linear growth portion, a+bx, from the curve and dividing the result by parameter a.

38. The system of claim 35, wherein at least the parameter a is determined, and wherein normalizing includes dividing the curve by parameter a.

39. The system of claim 35, wherein at least the parameters a, b and c are determined, and wherein normalizing includes subtracting off the linear growth portion, a+bx, from the curve and dividing the result by parameter c.

40. The system of claim 35, wherein processing includes determining the curvature at some or all points along the normalized curve.

41. The system of claim 40, wherein the intelligence module is further adapted to render a display of a plot of the curvature of the normalized curve.

42. The system of claim 32, wherein normalizing includes subtracting off a linear growth portion from the dataset.

43. The system of claim 32, wherein the intelligence module is further adapted to return the Ct value.

44. The system of claim 32, wherein the intelligence module is further adapted to display the Ct value.

45. The system of claim 32, wherein the pair of coordinate values represent an accumulation of amplified polynucleotide and a cycle number.

46. The system of claim 45, wherein the accumulation of amplified polynucleotide is represented by one of a fluorescence intensity value, a luminescence intensity value, a chemiluminescence intensity value, a phosphorescence intensity value, a charge transfer value, a bioluminescence intensity value, or an absorbance value.

* * * * *